United States Patent
Rao et al.

(10) Patent No.: US 6,630,996 B2
(45) Date of Patent: Oct. 7, 2003

(54) OPTICAL METHOD AND APPARATUS FOR INSPECTING LARGE AREA PLANAR OBJECTS

(75) Inventors: Nagaraja P. Rao, San Carlos, CA (US); Patrick D. Kinney, San Leandro, CA (US)

(73) Assignee: Real Time Metrology, Inc., Castro Valley, CA (US)

( * ) Notice: Subject to any disclaimer, the term of this patent is extended or adjusted under 35 U.S.C. 154(b) by 0 days.

(21) Appl. No.: 09/994,021

(22) Filed: Nov. 14, 2001

(65) Prior Publication Data

US 2002/0088952 A1 Jul. 11, 2002

Related U.S. Application Data

(60) Provisional application No. 60/297,660, filed on Jun. 12, 2001, and provisional application No. 60/249,000, filed on Nov. 15, 2000.

(51) Int. Cl.$^7$ .............................................. G01N 21/00
(52) U.S. Cl. ............................ 356/237.5; 356/237.1; 356/237.4
(58) Field of Search ...................... 356/237.1, 237.6, 356/600, 601, 609, 614, 1–4; 350/336–342; 250/201.1–201.4, 250

(56) References Cited

U.S. PATENT DOCUMENTS

| | | | |
|---|---|---|---|
| 3,790,287 A | 2/1974 | Cuthbert et al. ............ 356/120 |
| 4,342,515 A | 8/1982 | Akiba et al. ................ 356/237 |
| 4,373,805 A | * | 2/1983 | Mallinson ...................... 356/1 |
| 4,377,340 A | 3/1983 | Green et al. ................ 356/237 |
| 4,378,159 A | 3/1983 | Galbraith ..................... 356/237 |
| 4,482,424 A | 11/1984 | Katzir et al. ................ 156/626 |
| 4,569,695 A | 2/1986 | Yamashita et al. ............. 134/1 |
| 4,614,427 A | 9/1986 | Koizumi et al. ............. 356/237 |
| 4,655,592 A | 4/1987 | Allemand ................... 356/237 |
| 4,692,223 A | 9/1987 | Lampert et al. ............ 204/34.5 |
| 4,772,126 A | 9/1988 | Allemand et al. .......... 356/336 |
| 4,827,143 A | 5/1989 | Munakata et al. .......... 250/574 |
| 4,895,446 A | 1/1990 | Maldari et al. ............. 356/336 |
| 4,979,815 A | * | 12/1990 | Tsikos ........................... 356/1 |

(List continued on next page.)

OTHER PUBLICATIONS

W.P. Shaw and R.P. Sopher, "High Speed Automatic Particle Counter", IBM Technical Disclosure Bulletin, vol. 17, No. 9, Feb. 1975.

D.R. Oswald and D.F. Munro, "A Laser Scan Technique for Electronic Materials Surface Evaluation", Journal of Electronic Materials, vol. 3, No. 1, 1974.

H, Altendorfer, G. Kren et al. "Unpatterned Surface Inspection for Next Generation Devices", Solid State Technology, 1996, pp 93–99.

C. Bakolias and A.K. Forrest, "Dark Field, Scheimpflug Imaging for Surface Inspection", Machine Vision Applications in Industrial Inspection V, 1997, San Jose, CA SPIE.

(List continued on next page.)

*Primary Examiner*—Frank G. Font
*Assistant Examiner*—Sang H. Nguyen
(74) *Attorney, Agent, or Firm*—Westman, Champlin & Kelly

(57) ABSTRACT

An optical inspection module and method are provided for detecting particles on a surface of a substrate. The module includes a substrate holding position, wherein the surface of the substrate defines an object plane at the substrate holding position. A light source illuminates substantially the entire substrate surface. A lens is oriented to collect light reflected from the light beam path by the substrate surface and has a lens plane. A photodetector array has a plurality of pixels defining an image plane within a focal plane of the lens. Each pixel corresponds to an area on the surface and the plurality of pixels together form a field of view that covers substantially the entire surface.

52 Claims, 20 Drawing Sheets

U.S. PATENT DOCUMENTS

| | | | |
|---|---|---|---|
| 5,177,559 A | 1/1993 | Batchelder et al. | 356/237 |
| 5,189,481 A | 2/1993 | Jann et al. | 356/73 |
| 5,274,434 A | 12/1993 | Morioka et al. | 356/237 |
| 5,317,380 A | 5/1994 | Allemand | 356/338 |
| 5,355,212 A | 10/1994 | Wells et al. | 356/237 |
| 5,417,537 A | 5/1995 | Miller | 414/217 |
| 5,428,442 A | 6/1995 | Lin et al. | 356/237 |
| 5,450,205 A | 9/1995 | Sawin et al. | 356/382 |
| 5,479,252 A | 12/1995 | Worster et al. | 356/237 |
| 5,493,123 A | 2/1996 | Knollenberg et al. | 250/372 |
| 5,608,155 A | 3/1997 | Ye et al. | 73/28.01 |
| 5,628,954 A | 5/1997 | Sato | 438/16 |
| 5,629,768 A * | 5/1997 | Hagiwara | 356/237.1 |
| 5,631,733 A | 5/1997 | Henley | 356/237 |
| 5,659,390 A | 8/1997 | Danko | 356/237 |
| 5,777,729 A | 7/1998 | Aiyer et al. | 356/237 |
| 5,808,278 A | 9/1998 | Moon et al. | 219/506 |
| 5,854,674 A | 12/1998 | Lin | 356/237 |
| 5,859,698 A | 1/1999 | Chau et al. | 356/237 |
| 5,864,394 A | 1/1999 | Jordan, III et al. | 356/237 |
| 5,909,276 A | 6/1999 | Kinney et al. | 356/237 |
| 5,970,168 A | 10/1999 | Montesanto et al. | 382/149 |
| 5,987,160 A | 11/1999 | Harlow et al. | 382/145 |
| 6,084,664 A | 7/2000 | Matsumoto et al. | 356/237.4 |
| 6,115,120 A | 9/2000 | Moriya et al. | 356/337 |
| 6,169,602 B1 | 1/2001 | Taniguchi et al. | 356/399 |
| 6,292,260 B1 | 9/2001 | Lin et al. | 356/237.4 |
| 6,407,373 B1 * | 6/2002 | Dotan | 250/201.3 |

OTHER PUBLICATIONS

P. Burggraaf, "Patterned Wafer Inspection: Now Required!", Semiconductor International 17(14): pp 57–58 60, 1994.

D.L. Cavan, L.H. Lin et al., "Patterned Wafer Inspection Using Laser Holographer and Spatial Frequency Filter," Journal of Vacuum Science and Technology, 6(6) : pp 1934–1939, 1988.

R. Ceton, R. Goodner, et al., "Comparison of Patterned Wafer effect Detection Tools for General In–Line Monitors," IEEE/SEMI Advanced Semiconductor Manufacturing Conference, IEEE, 1996.

F.E. Doany, R.N. Singh et al., "Projection Display Throughput: Efficiency of Optical Transmission and Light–Source Collection," IBM Journal of Research and Development, 42(3) pp 387–400, 1998.

B.E. Dom, R. Bonner et al., "The P300: A System for Automatic Patterned Wafer Inspection," Machine Vision and Applications, vol. 1, pp 205–221, 1988.

R.S. Howland, K.B. Wells et al., "High–Speed Detection of Pattern Defects using Laser Scattering," Solid State Technology, 38(11): pp 123–126, 1995.

H. Moench, G. Derra et al., "Optimised Light Sources for Projection Displays,".

H. Moench, G. Derra et al., "Arc Stabilization for Short Arc Projection Lamps," SID 2000, Society of Information Display, 2000.

W. Morrow, R. Howland et al., "High–Speed Pattern Defect Detection Using Laser Scattering," Proceedings of the Institute of Environmental Sciences, pp 232–236, 1996.

A.K. Prasad, "Stereoscopic Particle Image Velocimetry," Experiments in Fluids, vol. 29, pp 103–116, 2000.

T. Reuter and U. Bohmler, "Using Laser–Based Patterned–Wafer Inspection for Memory and Logic Applications," Micro pp 89–95, 1999.

D. Roudin, P.D. Kinney et al., "New Sample Preparation Method for Improved Defect Characterization Yield on Bare Wafers," In–Line Methods and Monitors for Process and Yield Improvement, Santa Clara, CA, SPIE, 1999.

P. Sandland, "Automated Defect Inspection: Past, Present & Future," SPIE 1998.

S.O. Schellenberg, and U. Herdickerhoff, "Recognition of Defects of the Surfscan Installation Tencor 7600 Depending on the Situation and Size of the Defect," SPIE Conference on Microelectronic Manufacturing Yield, Reliability, and Failure Analysis IV, Santa Clara, CA SPIE 1998.

M.A. Taubenblatt and J.S. Batchelder, "Patterned Wafer Inspection Using Spatial Filtering for the Cluster Environment," Applied Optics, 31(17) pp 3354–3362, 1992.

B.M. Trafas, M. Nikoonahad et al. "Extendibility of Laser Scanning tools for Advanced Wafer Inspection," Proceedings of SPIE, 2439, pp 164–173, 1995.

L.S. Watkins, "Inspection of Periodic Patterns with Intensity Spatial Filters," Solid State Technology, 12(2), pp 35–38, 1969.

C.D. Allemand and J.J. Danko, "Heuristic Approach to Particle Detection on Virgin and Patterned Silicon Wafers," Optical Engineering, 34(2) pp 548–563, 1995.

K. Komatsu et al., "Automatic Macro Inspection Systems," SPIE Conference on Metrology, Inspection, and Process control for Microlithography XIII, Santa Clara, CA Mar. 1999, pp 764–771.

* cited by examiner

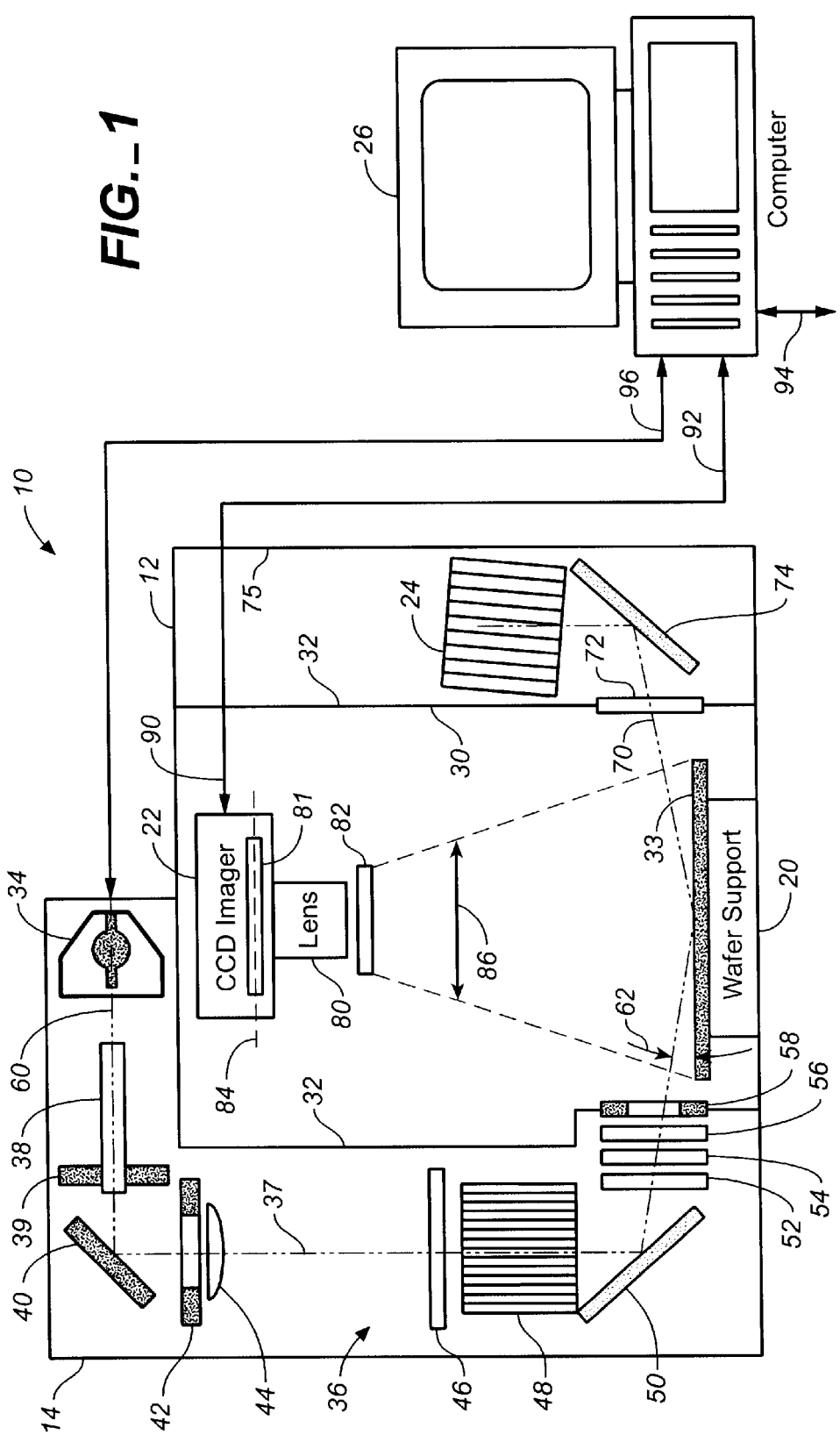
FIG._1

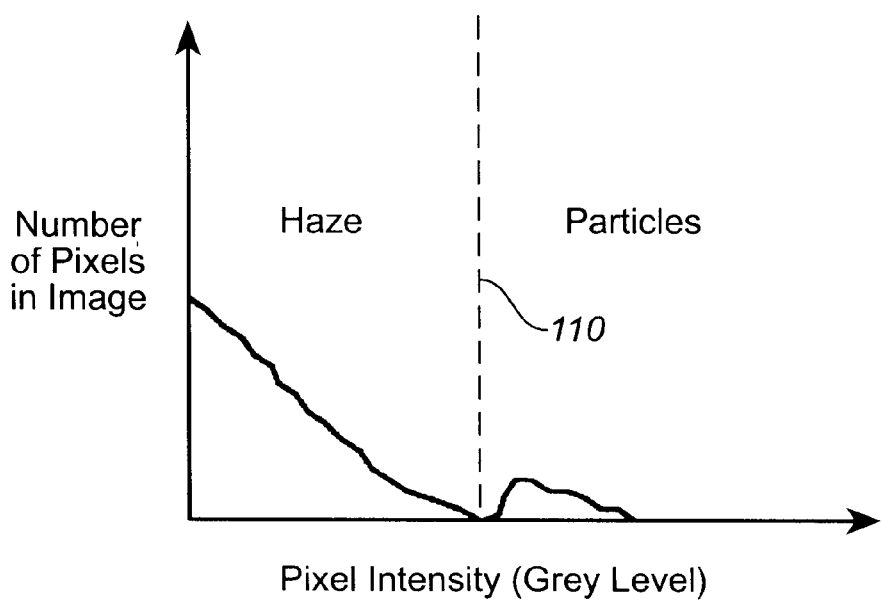
FIG._2

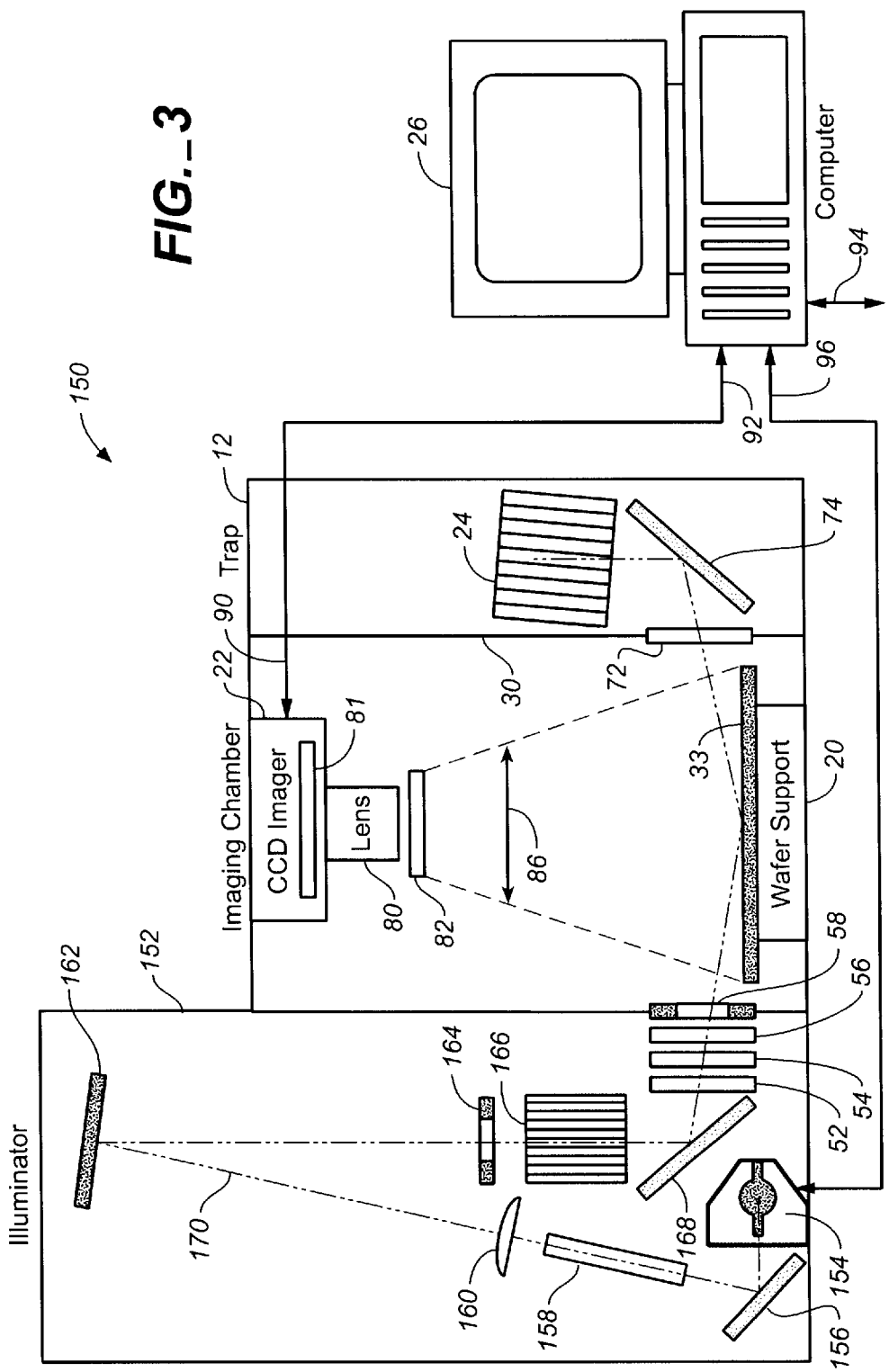

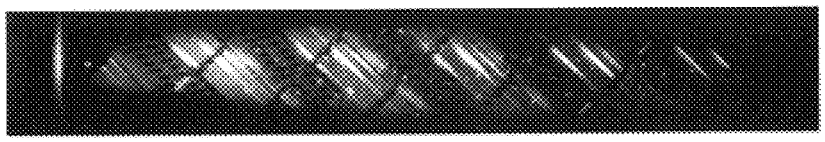
FIG._4A
FIG._4B
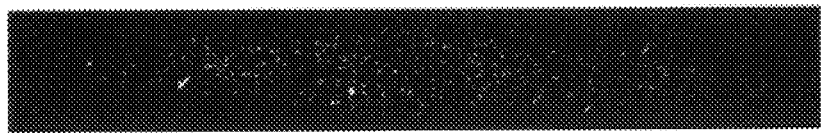
FIG._4C

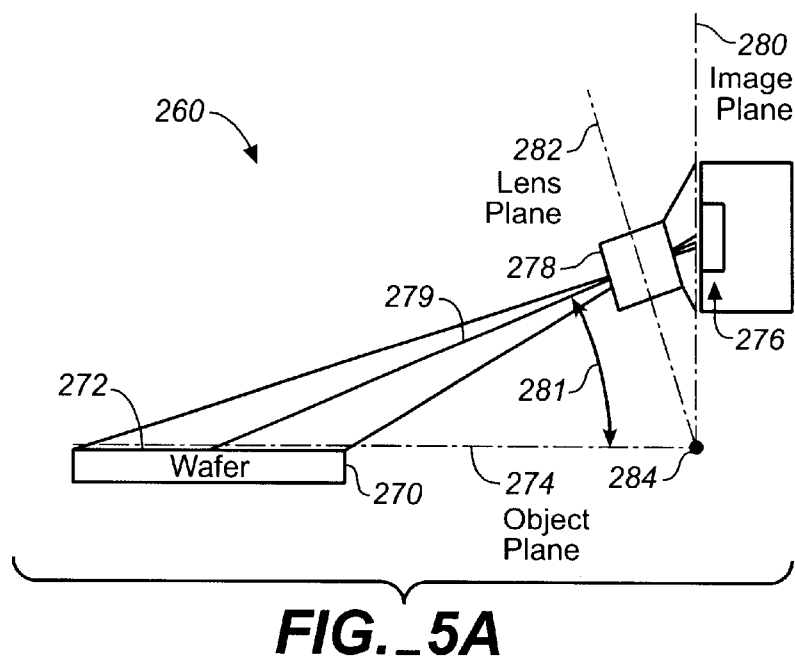
FIG._5A
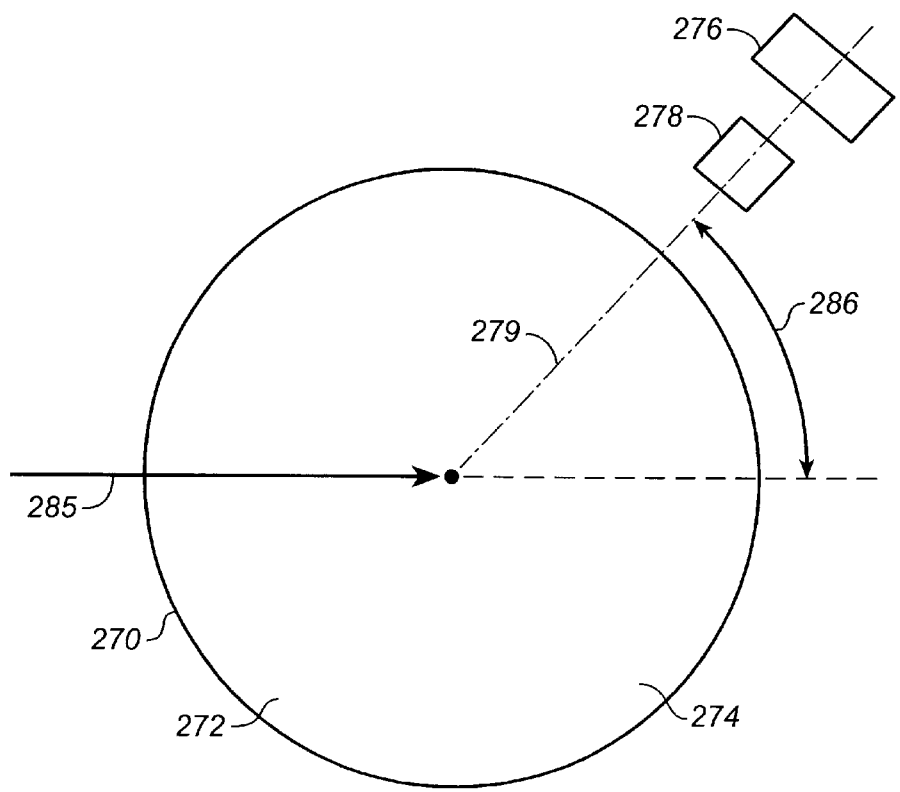
FIG._5B

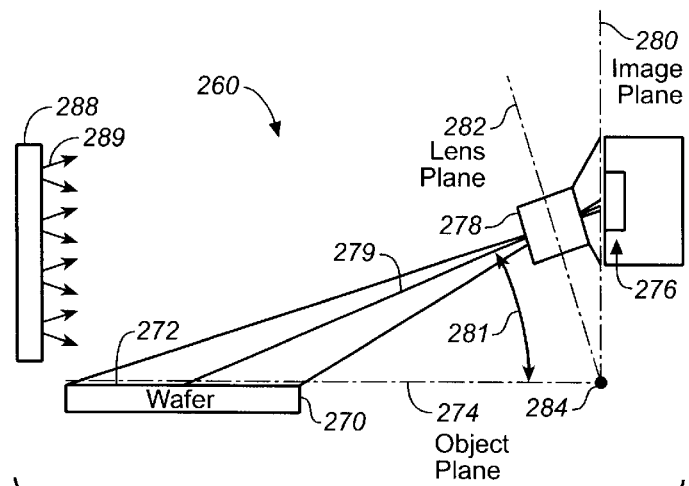
FIG._5C
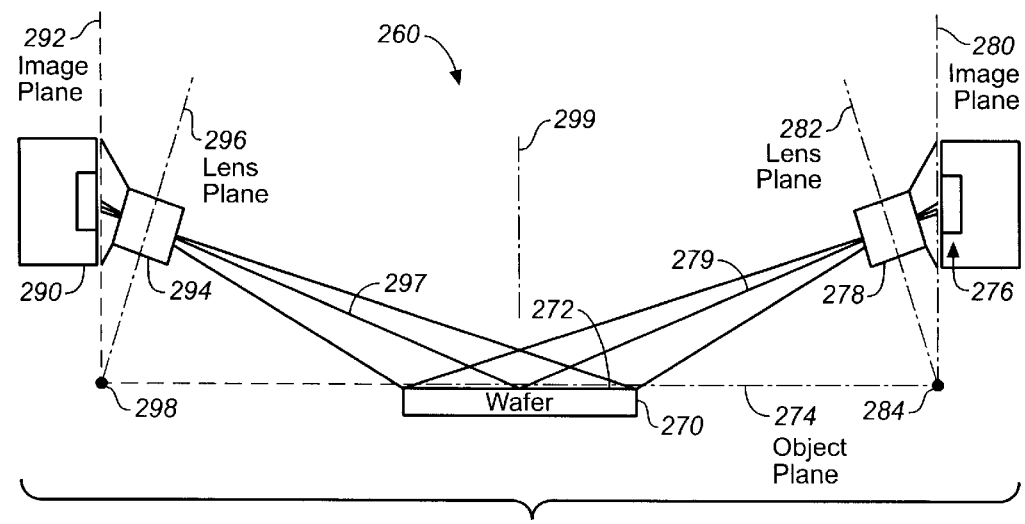
FIG._5D

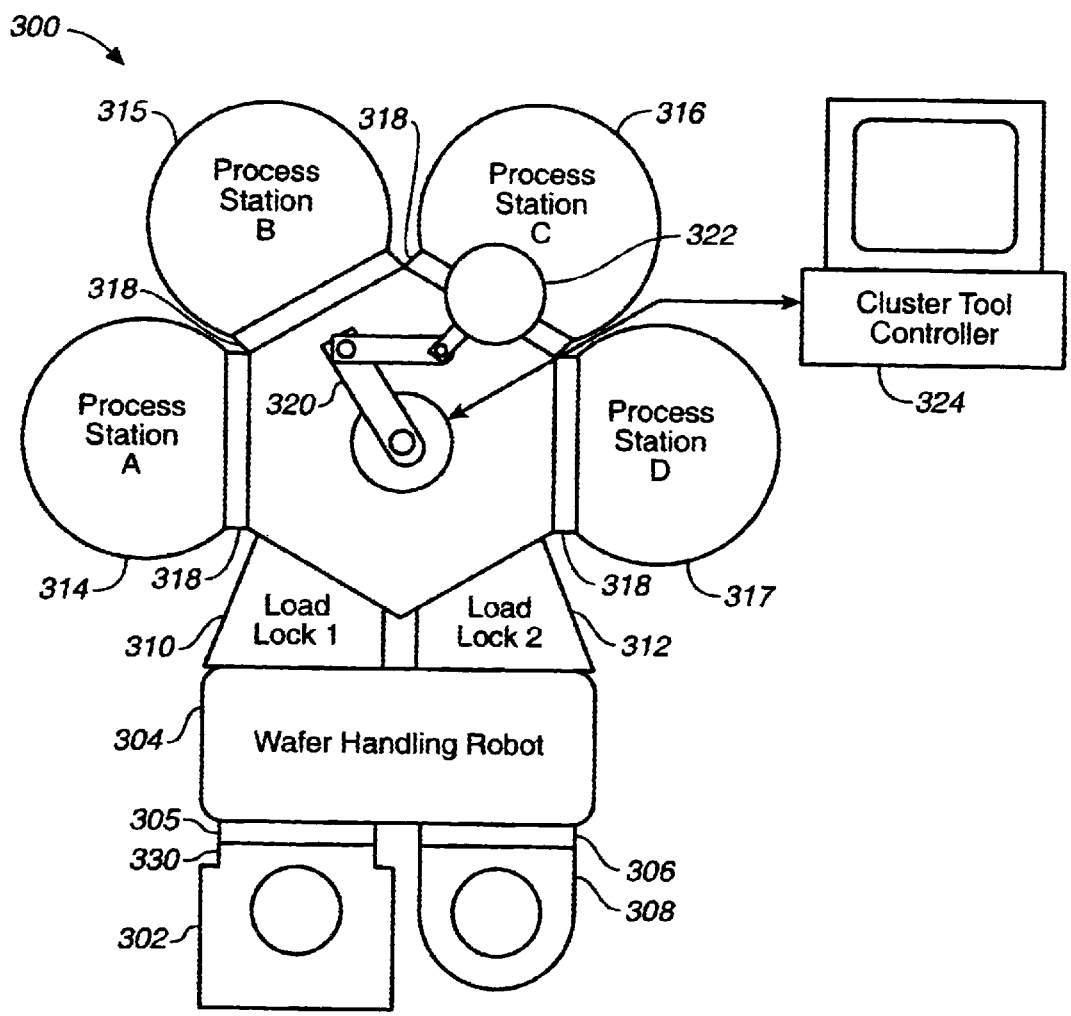
FIG._6

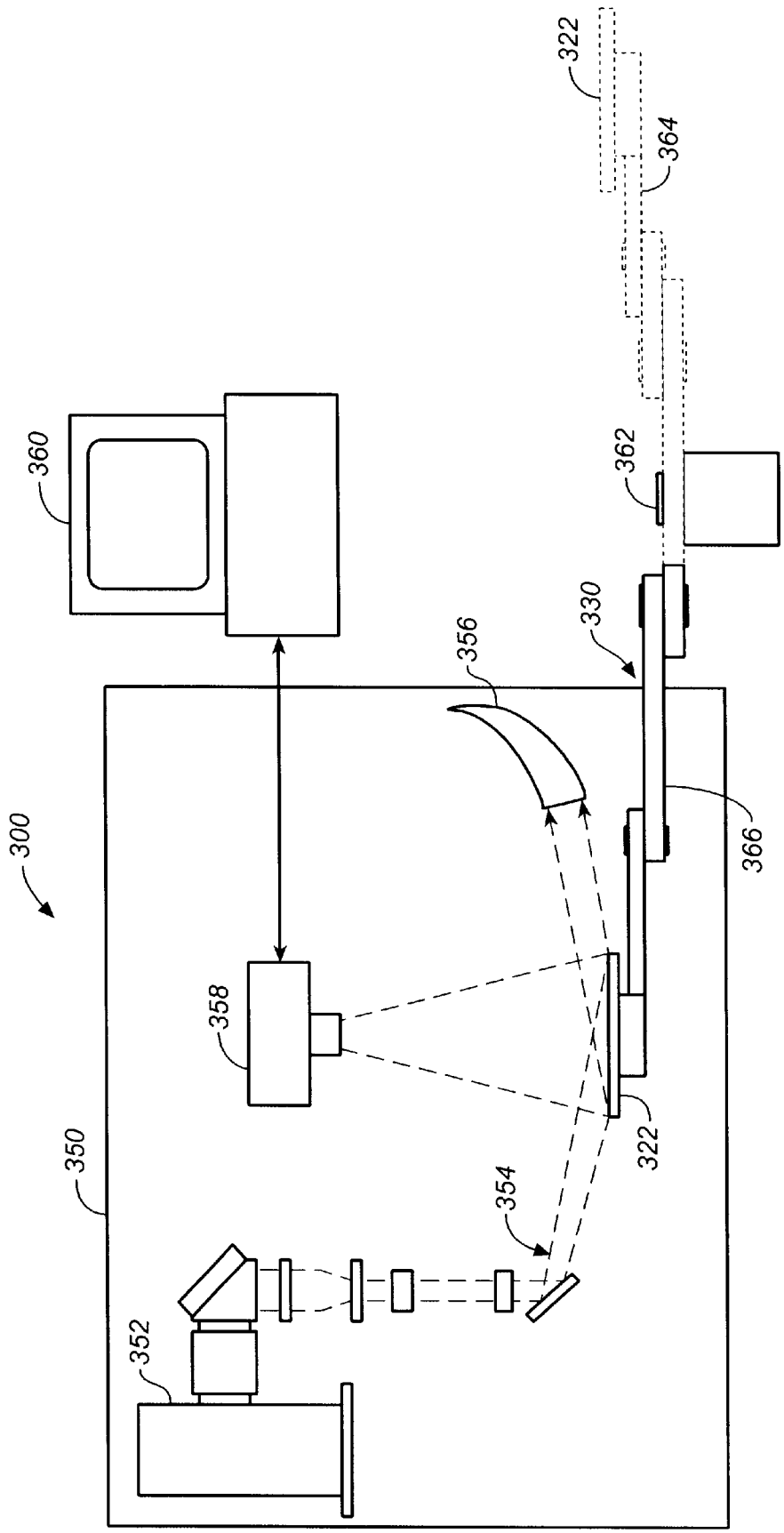

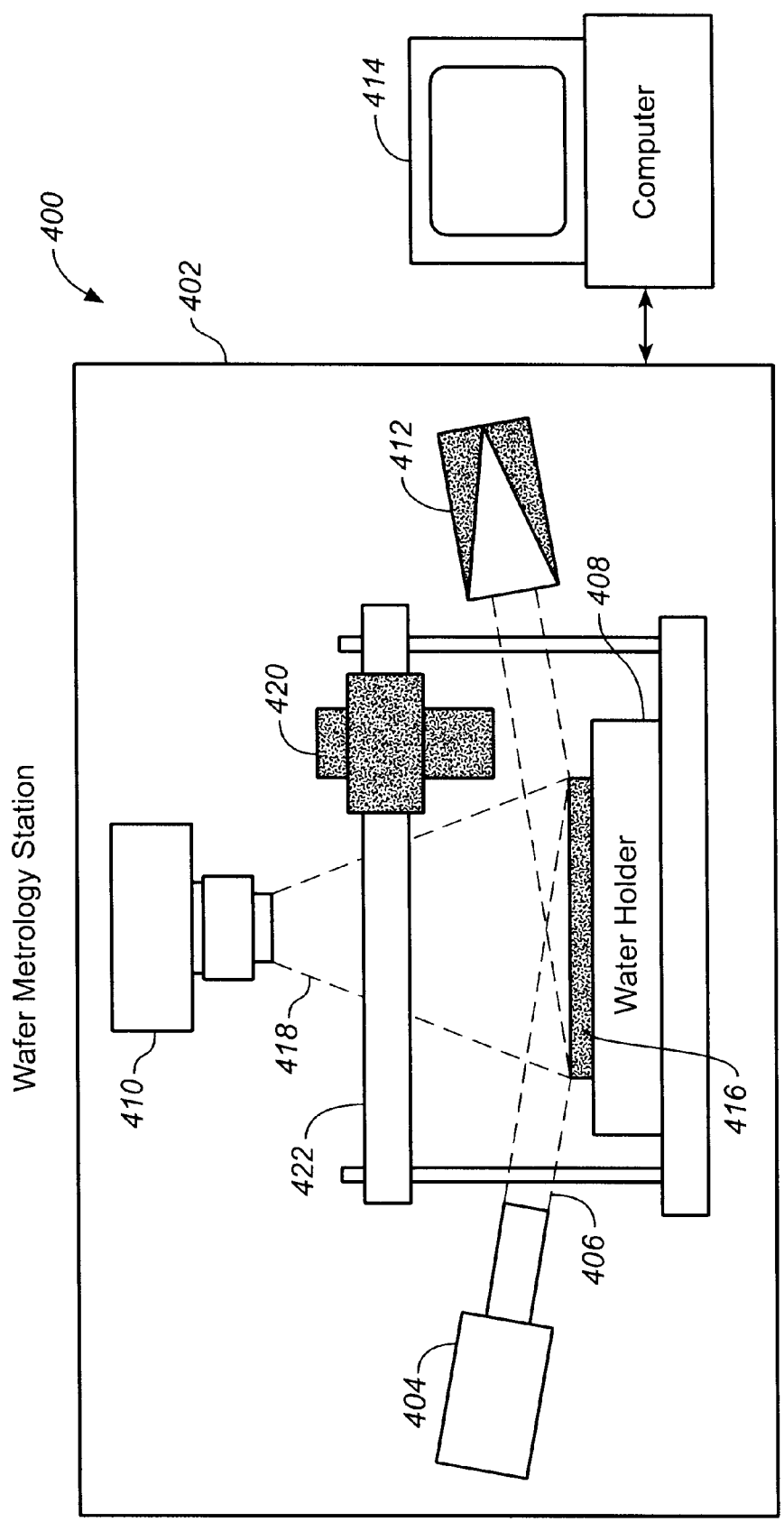
FIG._8

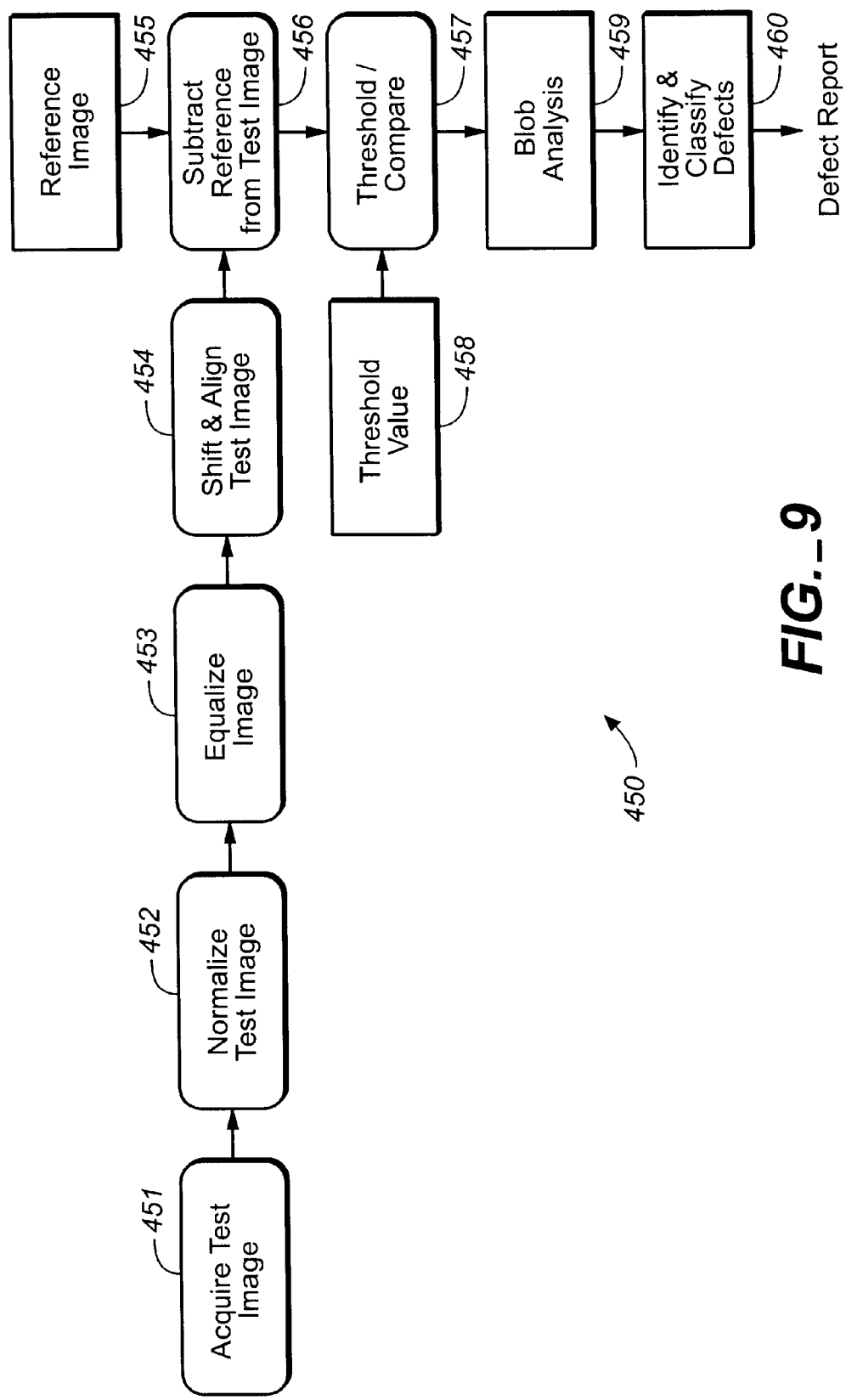
FIG._9

FIG._10A
FIG._10B
FIG._10C
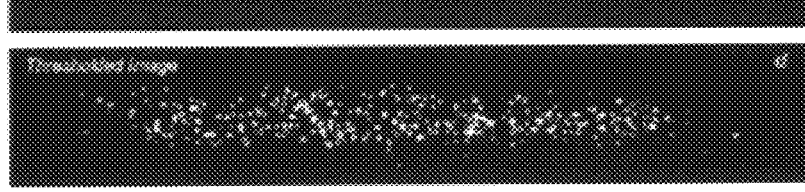
FIG._10D

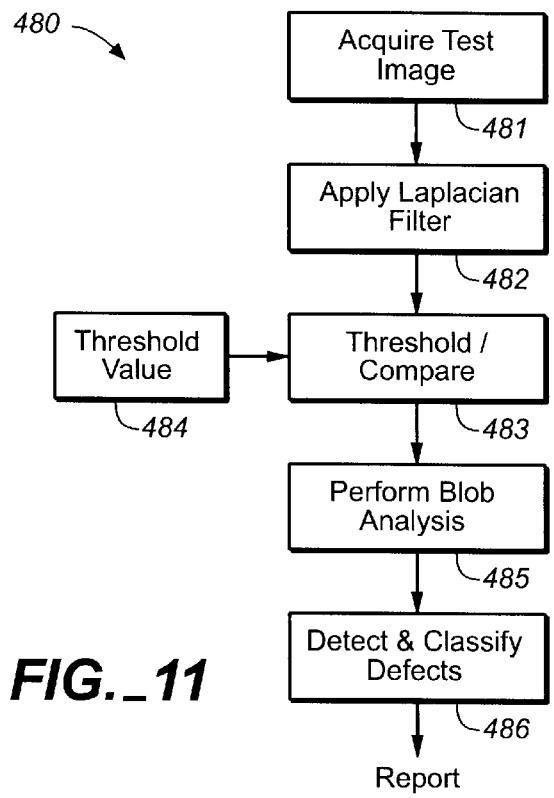
FIG._11
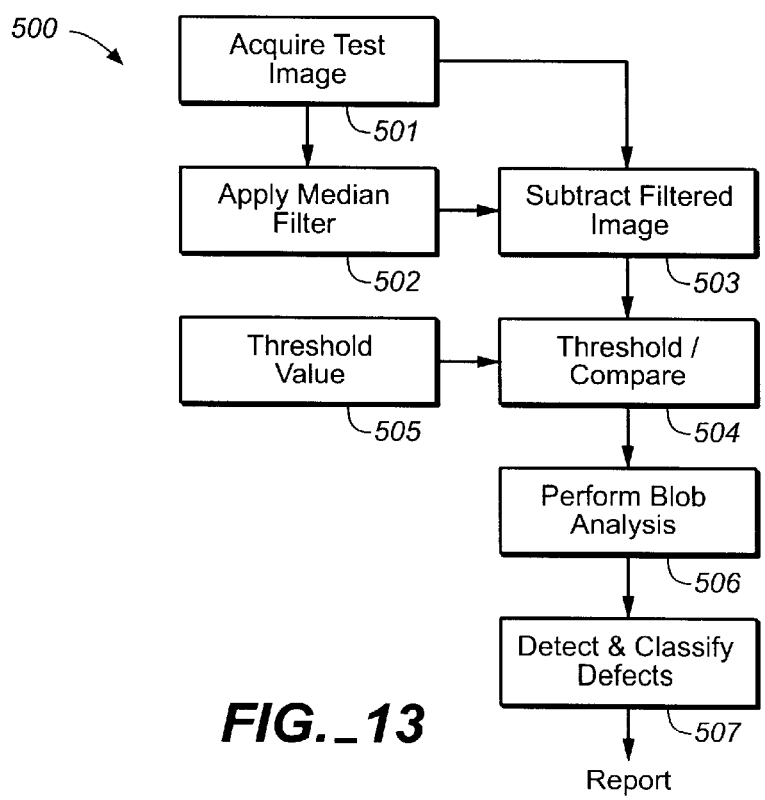
FIG._13

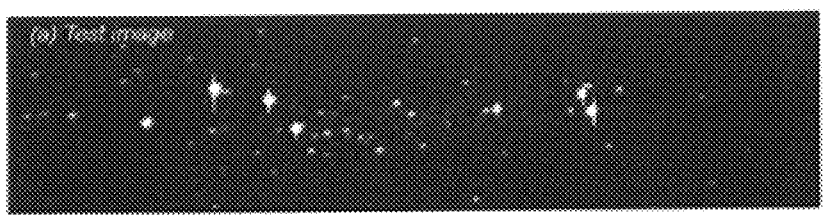
FIG._12A
FIG._12B
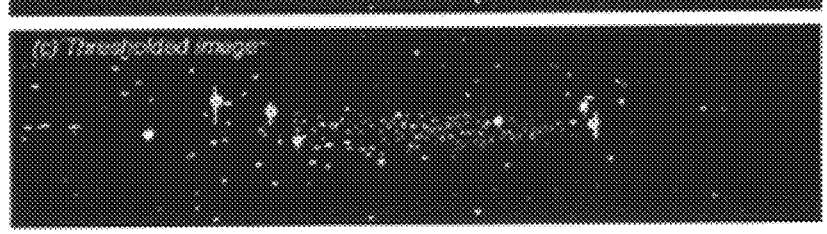
FIG._12C

FIG._14A
FIG._14B
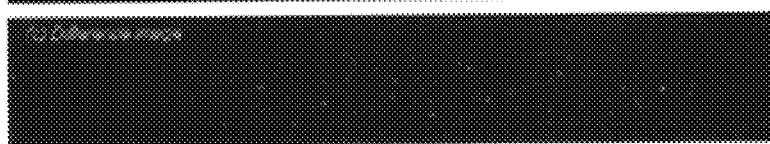
FIG._14C
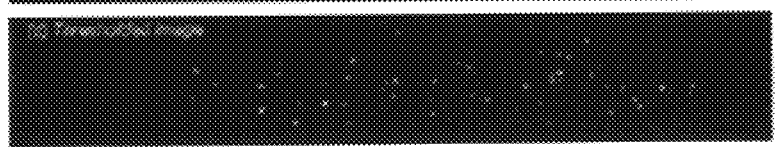
FIG._14D

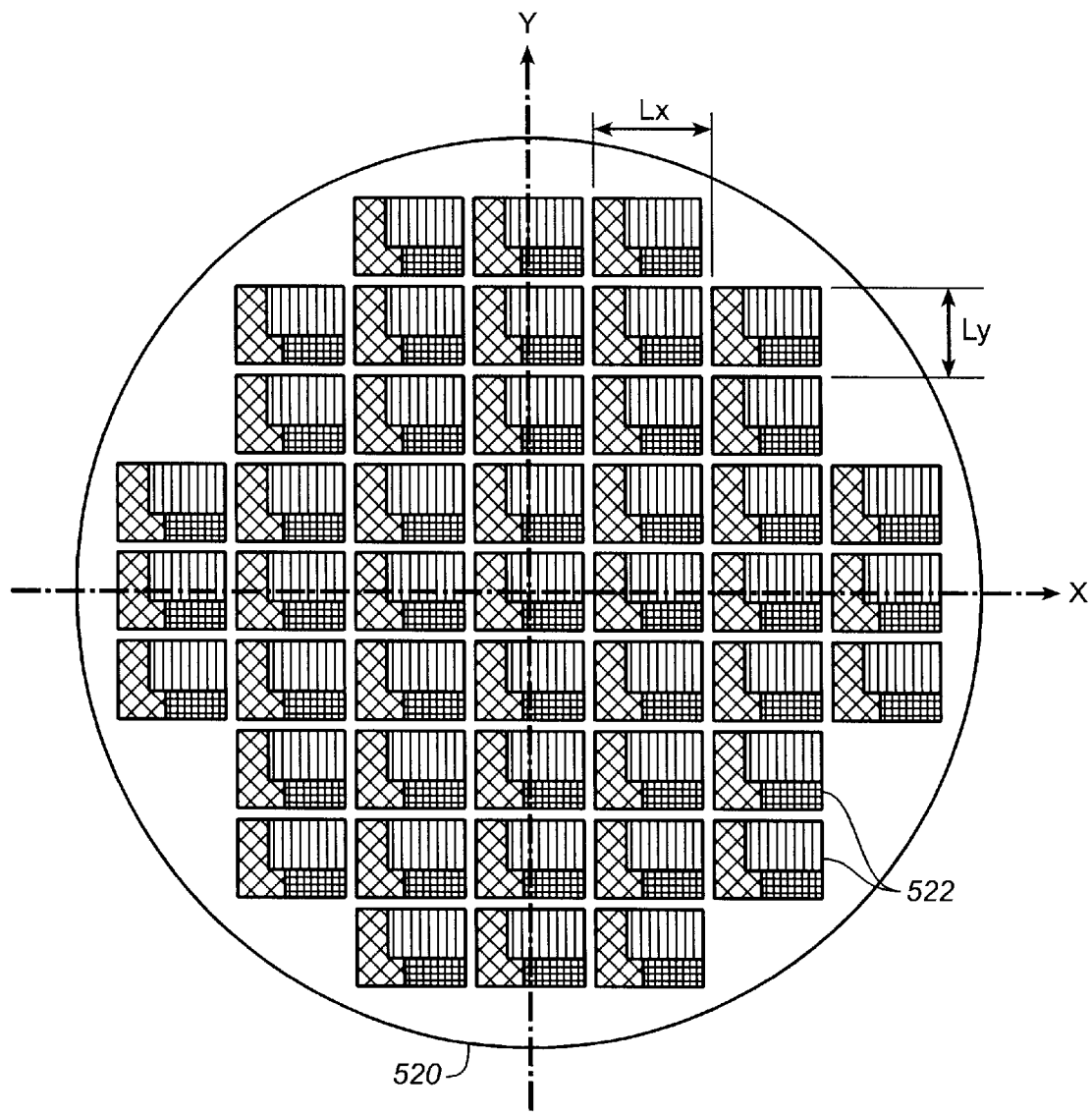
FIG._15

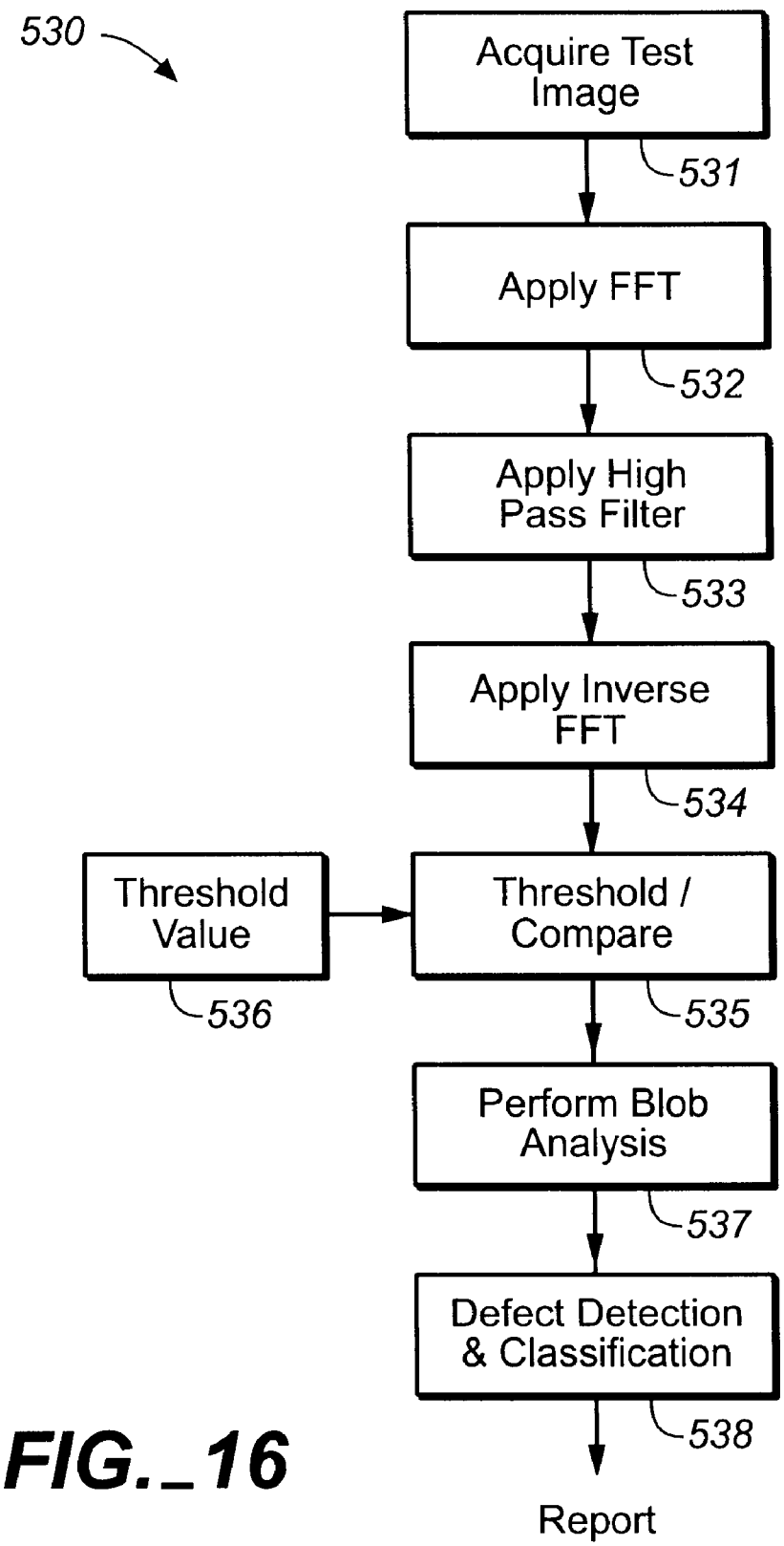
FIG._16

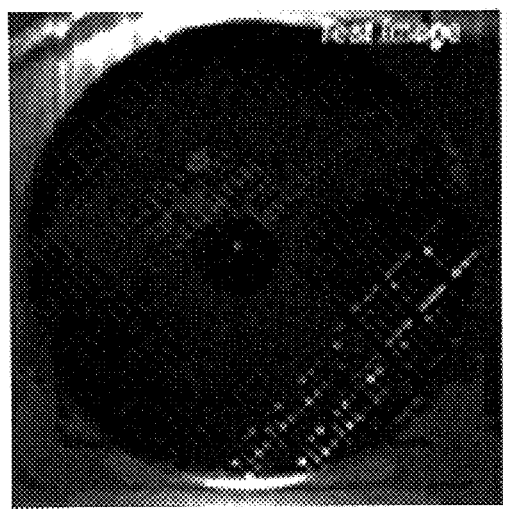
FIG._17A   FIG._17B

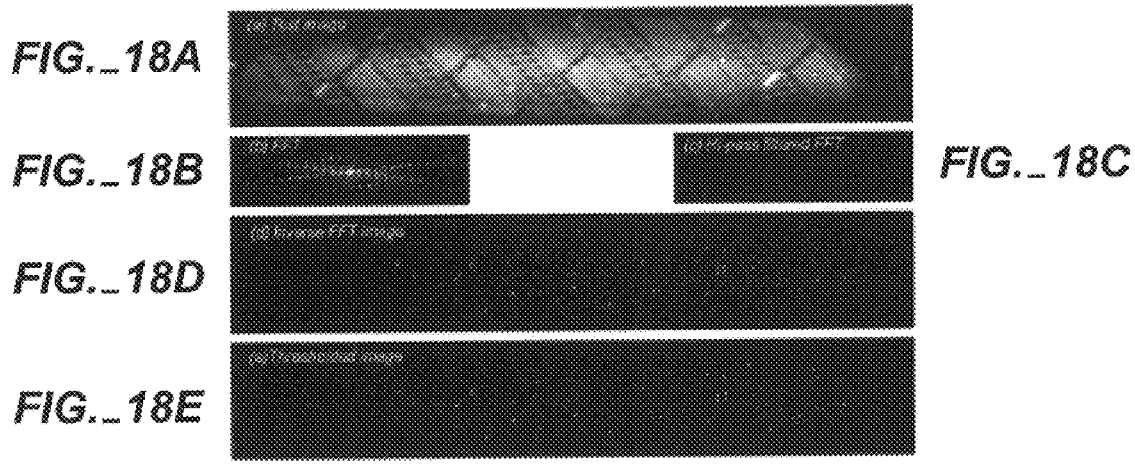
FIG._18A
FIG._18B  FIG._18C
FIG._18D
FIG._18E

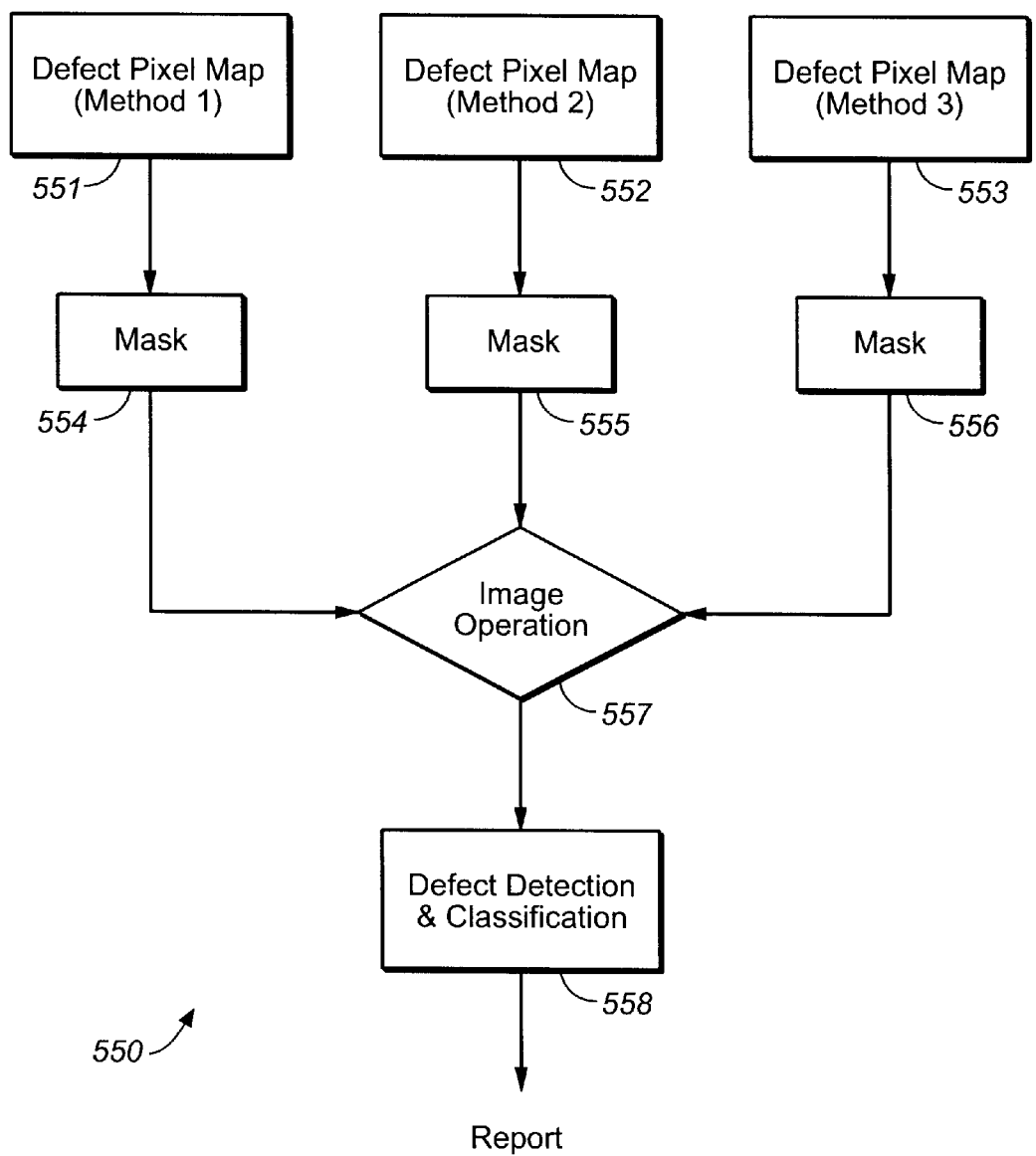
FIG._19

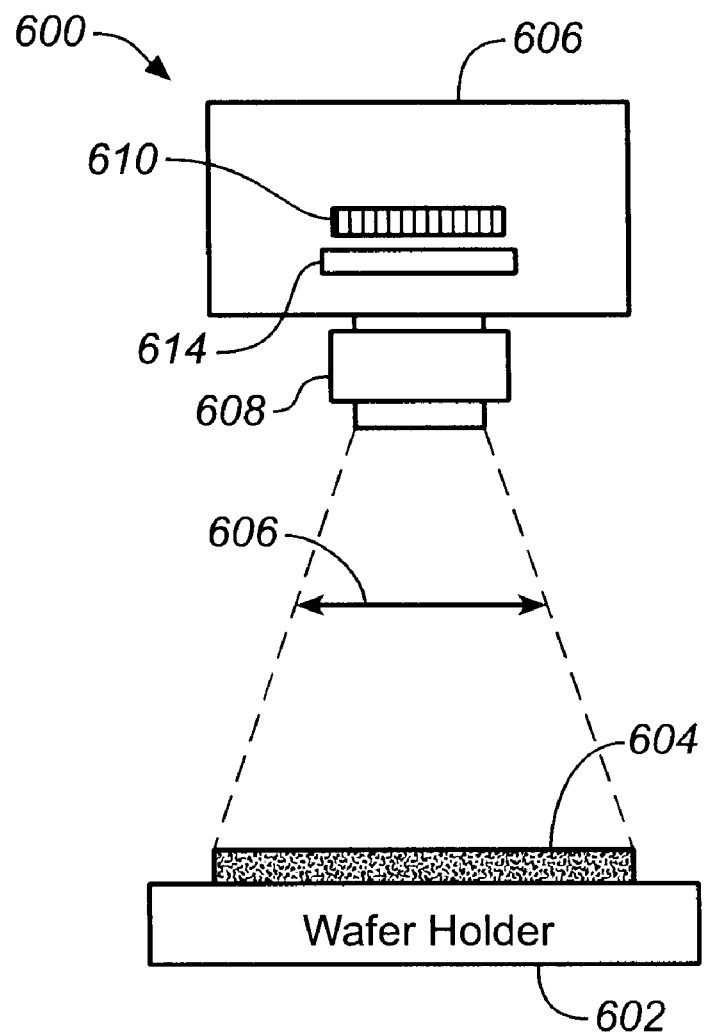
FIG._20

OPTICAL METHOD AND APPARATUS FOR INSPECTING LARGE AREA PLANAR OBJECTS

CROSS-REFERENCE TO RELATED APPLICATIONS

The present application is based on and claims the benefit of U.S. provisional patent application Serial No. 60/249,000, filed Nov. 15, 2000, and U.S. provisional patent application Serial No. 60/297,660, filed Jun. 12, 2001, the contents of which are hereby incorporated by reference in their entirety.

FIELD OF THE INVENTION

The present invention relates to optical metrology for large-area substrates. In particular, the present invention relates to methods and apparatus used to detect defects and particle contamination on such substrates.

BACKGROUND OF THE INVENTION

It is well known that the presence of contaminant particles on the surface of electronic substrates such as semiconductor wafers can lead to the formation of defects during the microelectronics fabrication process. In order to maintain high manufacturing yield and thus low manufacturing costs, it is necessary that contaminated wafers be identified during the manufacturing process. Several automated optical inspection systems are commercially available for the purpose of detecting particles and defects on wafers and like substrates.

In general, wafer inspection systems can be divided into two broad classes: (i) those that detect particles by light scattering as the wafer surface is scanned by a laser; and (ii) those that detect particles and defects through processing of a captured digital image. In both these approaches, generally only a small portion of the wafer is illuminated at a time, therefore requiring the wafer to move relative to the illuminating beam to enable the entire surface to be inspected. The laser light scattering systems have traditionally been used mainly for inspecting un-patterned wafers, while the digital image processing systems have been used mainly for inspecting patterned wafers. Recently, laser scanning light scattering systems have also been used for detecting defects on patterned wafers.

Wafer inspection tools such as those described above have been configured as specialized stand-alone inspection systems designed to provide sensitivity to extremely small defects and particles, and are thus complex in design and expensive. In semiconductor production fabs, patterned wafer inspection tools are used to monitor defects on product wafers. Many of these tools are digital image processing systems which typically use microscope objectives to image a small portion of the wafer at a time. The pixel size is typically on the order of the minimum feature size, requiring an enormous number of pixels to be processed. For example, detection of 0.5 micrometer ($\mu$m) minimum defects on a 150 millimeter (mm) wafer requires about $2.8 \times 10^{11}$ pixels. For 200 mm wafers the corresponding number of pixels to be processed is on the order of $5 \times 10^{11}$ or higher. Since the inspection throughput of such systems is fairly low, only a few wafers per lot are normally inspected. Additionally, the high cost of these inspection systems necessarily means that the number of such systems present in production lines used in microelectronics manufacture is low, with the result that inspections for particles and defects are relatively few and far between. Since a very large number of process steps are involved in the manufacture of microelectronics and semiconductor devices, a sparse sampling of wafers in the production line may lead to contaminated wafers remaining undetected for a long period of time, leading to lower yield and increased rework costs.

Many of the above particle detection systems described above use specialized signal processing techniques to minimize background scatter when inspecting patterned microelectronic substrates. For laser scanning light-scattering systems, a locally varying threshold combined with periodic feature elimination has been used to distinguish defects from the background pattern. The pattern features may be eliminated by comparing signals from adjacent repeating patterns in a die-to-die comparison. Examples of such systems have been disclosed in U.S. Pat. Nos. 5,864,394, and in 5,355,212.

The image processing based inspection systems also have used image-to-image comparison for eliminating the background due to the pattern. The reference image used for comparison could be (i) an image of a duplicated region such as an adjacent die, (ii) an image of a known good part stored in an image database, or (iii) an image created from computer-aided design (CAD) rule data.

Several inspection systems based on optical pattern filtering using Fourier masks have also been described in literature for the inspection of patterned wafers having periodic features. These systems are based on the idea that periodic features on the wafer being inspected can be filtered out of an image in the optical Fourier transform plane while random defect features are transmitted. This technique was originally developed for inspecting masks, and more recently has been used for patterned wafer inspection. The substrate with periodic features is illuminated by a coherent plane wave and imaged by a Fourier transform lens, which creates a diffraction pattern image at its focal plane—the Fourier plane. Periodic features on the object are mapped onto bright, intense spots in the diffraction pattern. A transparent plate with opaque regions is placed in the Fourier plane so that the opaque portions mask the bright spots originating from periodic features. The light passing through the transparent regions of the mask is collected by a second Fourier transform lens creating an image on its focal plane, which is recorded by a camera. This selective masking (spatial filtering) in the Fourier plane creates an image in which the periodic background pattern has been filtered out, enabling defect features to be more easily detected.

It should be noted that such Fourier filtering has been generally considered impractical when the repeat distances for the patterns is large compared to the wavelength of light used. In this case, the diffraction pattern contains many closely spaced spots arising from multiple diffracted orders, and fabricating and aligning a suitable mask poses difficulties. Furthermore, the available aperture for passing defect features is also limited.

In the case of prior art wafer inspection systems implementing optical pattern filtering, the wafer is usually imaged at high magnification with sub-micron pixels, and the repeating distances within a die are generally on the order of a few wavelengths of light. In this situation Fourier filtering is more easily implemented. Imaging at high magnification necessitates the processing of a very large number of images ($\sim 10^5$) or pixels ($\sim 10^{11}$) per wafer. Considering the large number of images to be processed, it is no surprise that prior art systems have implemented Fourier filtering via optical hardware, i.e. using Fourier transform optics and masks, since this enables the Fourier transform and resulting filtering to be accomplished literally at the "speed of light" and therefore permits a reasonable throughput. However, at high magnification since only a portion of a die is inspected at a time, these techniques are generally limited to the inspection of patterned wafers having significant intra-die periodicity, such as memory chips. Additionally, inspection of wafers with different patterns requires different hardware masks which are cumbersome to use and also add to the tool set-up time and cost. Finally, the implementation of Fourier filtering in hardware generally requires the use of coherent light, therefore restricting practical illumination sources to lasers.

More recently, an alternate technique for inspecting patterned semiconductor wafers has been disclosed in Aiyer et al, U.S. Pat. No. 5,777,729 entitled "Wafer Inspection Method and Apparatus Using Diffracted Light." This method appears to be based on detecting bright, highly directional diffracted light from the pattern structures on the wafer and is useful for detecting large macro-defects. The relatively low sensitivity associated with macro-defect inspection may not meet the requirements of present day semiconductor manufacturers interested in detecting sub-micron defects, associated with the sub-micron feature sizes found on the state-of-the-art integrated circuits.

There is thus a continuing need for wafer inspection systems that are capable of providing more rapid feedback regarding process excursions, and perhaps even providing prior warning of a process excursion about to occur. A high-speed patterned wafer inspection system could be used to measure every product wafer and thus enable wafer-to-wafer process control within the production line. New and improved inspection technology is desired that is flexible enough to handle the varied demands of the semiconductor industry such as high speed inspection of sub-micron defects.

SUMMARY OF THE INVENTION

One embodiment of the present invention is directed to an optical inspection module for detecting particles on a surface of a substrate. The module includes a substrate holding position, wherein the surface of the substrate defines an object plane at the substrate holding position. A light source illuminates substantially the entire substrate surface. A first lens is oriented to collect light reflected from the light beam path by the substrate surface and has a lens plane. A first photodetector array has a plurality of pixels defining an image plane within a focal plane of the first lens. Each pixel corresponds to an area on the surface and the plurality of pixels together form a field of view that covers substantially the entire surface. The lens plane and the image plane are non-parallel to the object plane.

Another embodiment of the present invention is directed to an integrated optical inspection module. The module includes first and second measurement instruments and a substrate holder for holding a substrate having a surface. The first measurement instrument detects defects on the substrate surface and includes a light source having a light beam port and a light beam path extending from the light beam port to the substrate holding position and illuminating substantially the entire substrate surface on the substrate holder. A lens is oriented to collect light reflected from the light beam path by the substrate surface. A photodetector array has a plurality of pixels defining an image plane within a focal plane of the lens. Each pixel corresponds to an area on the substrate surface and the plurality of pixels together form a field of view that covers substantially the entire substrate surface. The second measurement instrument is integrated into the module with the first measurement instrument and includes a sensor oriented for sensing a physical characteristic of the substrate surface.

Another embodiment of the present invention is directed to an optical inspection module including a light source and a substrate holding position for holding a substrate having a surface. The light source produces an excitation light beam in a first wavelength range. A light beam path extends from the light source to the substrate holding position and illuminates substantially the entire substrate surface at the substrate holding position with the excitation light beam, whereby compounds on the substrate surface absorb energy from the excitation light beam and emit photons of lower energy in a second, different wavelength range. The module further includes a lens and a photodetector array having a plurality of pixels defining an image plane within a focal plane of the lens. Each pixel corresponds to an area on the substrate surface and the plurality of pixels together form a field of view that covers substantially the entire substrate surface. An optical filter is positioned within an optical path from the substrate to the photodetector array, through the lens, which entirely blocks light reflected from the substrate surface in the first wavelength range and transmits light emitted from the substrate surface in the second wavelength range.

Another embodiment of the present invention is directed to a method of inspecting a surface of a substrate. The method includes: (a) illuminating substantially the entire substrate surface with a light beam; (b) applying light reflected from the light beam by any defects or other features on the substrate surface to a photodetector array having a plurality of pixels, wherein each pixel corresponds to a unit area on the surface and the plurality of pixels together have a field of view covering substantially the entire surface; (c) producing a digital test image having a plurality of pixels with intensities that are functions of intensities of the reflected light applied to corresponding pixels in the photodetector array; (d) applying a digital convolution filter to the digital test image to produce a filtered test image having a plurality of pixels; and (e) comparing intensity of pixels of the filtered test image to a respective intensity threshold value.

Another embodiment of the present invention is directed to a method of inspecting a surface of a substrate. The method includes: (a) illuminating substantially the entire substrate surface; (b) applying light reflected by any defects or other features on the substrate surface to a photodetector array having a plurality of pixels, wherein each pixel corresponds to a unit area on the surface and the plurality of pixels together have a field of view covering substantially the entire surface; (c) producing a digital test image having a plurality of pixels, wherein each pixel has an intensity that is a function of an intensity of the reflected light applied to a corresponding pixel in the photodetector array; (d) for each pixel in the digital test image, producing a corresponding pixel in a reference image having an intensity equal to a mathematical function of the intensities of a plurality of the pixels in the digital test image that surround that pixel; (e) subtracting the reference image from the digital test image to produce a difference image having a plurality of pixels; and (f) comparing intensity of pixels in the difference image to a respective intensity threshold value.

Another embodiment of the present invention is directed to a method of inspecting a surface of a patterned substrate having a substrate surface with a background pattern. The method includes: (a) illuminating substantially the entire substrate surface; (b) applying light reflected from the substrate by any defects or other features on the substrate surface to a photodetector array having a plurality of pixels, wherein each pixel corresponds to a unit area on the surface and the plurality of pixels together have a field of view covering substantially the entire surface; (c) producing a digital test image having a plurality of pixels, wherein each pixel has an intensity that is a function of an intensity of the reflected light applied to a corresponding pixel in the photodetector array; (d) applying a digital fast Fourier transform to the digital test image to produce a transform image; (e) filtering the transform image to produce a filtered transform image in which features produced in the transform image by repeating patterns of the substrate surface are removed; and (f) applying a digital inverse fast Fourier transform to the filtered image to produce a re-created image of the substrate surface with the repeating patterns filtered out.

Yet another embodiment of the present invention is directed to a method of inspecting a surface of a patterned substrate having a substrate surface with a background pattern. The method includes: (a) illuminating substantially the entire substrate surface with a light beam; (b) applying non-specularly reflected light that is scattered from the light beam by any defects on the substrate surface to a photodetector array having a plurality of pixels, wherein each pixel corresponds to a unit area on the surface and the plurality of pixels together have a field of view covering substantially the entire surface; (c) producing a digital test image having a plurality of pixels, wherein each pixel has an intensity that is a function of an intensity of the scattered light applied to a corresponding pixel in the photodetector array; (d) applying a first image filtering process to the digital test image to produce a first defect pixel map; (e) applying a second image filtering process to the digital test image to produce a second defect pixel map; and (f) combining each pixel of the first defect pixel map with a corresponding one of the pixels in the second defect pixel map to produce a corresponding pixel in a combined defect pixel map.

BRIEF DESCRIPTION OF THE DRAWINGS

FIG. 1 is a schematic representation of a large area optical inspection module for detecting particles and other features on a substrate according to one embodiment of the present invention.

FIG. 2 is histogram illustrating an example of the number of pixels in a substrate image as a function of pixel intensity.

FIG. 3 is a schematic representation of an optical inspection module having an alternative illuminator.

FIGS. 4A–4C are photographs showing a sequence of images obtained by inspecting a patterned wafer through the detection of de-polarized scattered light with the module shown in FIG. 1.

FIG. 5A is a schematic illustration of an optical inspection module for imaging at an oblique angle to the substrate surface.

FIG. 5B is a schematic top plan view of the optical inspection module shown in FIG. 5A, as viewed from above the substrate.

FIG. 5C is a schematic illustration of an optical inspection module for brightfield imaging at an oblique angle to the substrate surface, wherein the substrate is illuminated by a uniformly illuminated panel.

FIG. 5D is a schematic illustration of an optical inspection module for imaging at two oblique angles at one time.

FIG. 6 is a schematic illustration of a multi-process cluster tool system in which an inspection module is integrated into a load/unload port of the system, according to one embodiment of the present invention.

FIG. 7 is a schematic illustration of the inspection module shown in FIG. 6, which shows the insertion of a substrate by a wafer handling robot.

FIG. 8 is a schematic illustration of an integrated metrology station having two measurement instruments according to one embodiment of the present invention.

FIG. 9 is a flow chart which shows an image acquisition and analysis process used to extract defects from a test image using a previously stored reference image according to one embodiment of the present invention.

FIGS. 10A–10D are photographs showing a sequence of images produced in the process shown in FIG. 9 for the case of a patterned wafer.

FIG. 11 is flow chart illustrating an example of an image acquisition and analysis process which uses a convolution filter.

FIGS. 12A–12C are photographs showing a sequence of images produced in the process shown in FIG. 11 for the case of a bare wafer.

FIG. 13 is a flow chart illustrating an example of an image acquisition and analysis process which uses spatial filtering.

FIGS. 14A–14D are photographs showing a sequence of images where spatial filtering has been used according to the process shown in FIG. 13 for the case of a patterned wafer.

FIG. 15 is schematic representation of a typical patterned wafer showing the regular placement of individual die.

FIG. 16 is flow chart illustrating an image acquisition and analysis process which uses computerized frequency filtering to detect defects on patterned wafers.

FIG. 17A shows a test image of a patterned 200 millimeter wafer.

FIG. 17B shows the corresponding frequency spectrum image obtained by computing a fast Fourier Transform of the test image shown in FIG. 17A.

FIGS. 18A–18E are photographs showing a sequence of images where computer pattern filtering has been used to detect particles on a 150 millimeter patterned wafer according to the method shown in FIG. 16.

FIG. 19 is flow chart which shows an example procedure for combining results from two or more image acquisition and analysis processes.

FIG. 20 is schematic illustration of a portion of an inspection module having a programmable LCD mask according to another alternative embodiment of the present invention.

DETAILED DESCRIPTION OF THE PREFERRED EMBODIMENTS

1. Optical Inspection Module

FIG. 1 is a schematic representation of a large area optical inspection module 10 according to one embodiment of the present invention. Inspection module 10 is useful for detecting particles and other defects on large substrates such as semiconductor wafers, flat panel displays, magnetic recording discs and electronic packages substrates, for example. Inspection module 10 includes enclosure 12, illuminator 14, substrate holder 20, imaging camera 22, light trap 24 and computer controller 26.

Enclosure 12 is preferably light-proof and has light-absorbing internal surfaces 30 for minimizing deleterious effects of internal and external stray light during inspection. In one embodiment, enclosure 12 forms a vacuum chamber, and the components internal to enclosure 12 are vacuumcompatible components. Enclosure 12 can have one or more walls 32 for forming compartments that optically and physically isolate various components of module 10. Enclosure 12 can further include an entrance, gate or door (not shown) through which substrates, such as substrate 33, are loaded into and unloaded out of enclosure 12.

Illuminator 14 is housed within a first compartment of enclosure 12. Illuminator 14 includes light source 34 and beam shaping and conditioning components 36 which define a light beam path 37. Beam shaping and conditioning components 36 include optical integrator mixer rod 38, baffle 39, cold mirror 40, aperture 42, lenses 44 and 46, stray light baffle 48, cold mirror 50, polarizing filter 52, band pass filter 54, wedge filter 56 and mask 58. Mirrors 40 and 50 are provided in the light beam path 37 so that beam conditioning components 36 can be arranged in a compact space to reduce the overall size of illuminator 14.

Depending on the application, different types of light sources 34 can be used. For inspection based on light scattering detection, monochromatic laser light may be used when it is necessary to minimize chromatic aberration in the imaging optics. In some cases, laser light is easier to collimate and its use also enables better discrimination between scattered light and external stray light by incorporating a narrow laser band pass filter into the path of the detected light. The laser band-pass filter transmits light only in the illuminating laser wavelength range while rejecting stray light in all other wavelengths. Laser light may also be advantageous for photo-luminescence measurements, as it is easier to reject the excitation light using a narrow band-stop filter, such as a holographic notch filter. Lasers also have a short warm-up time and generally have a long operational life, often greater than 10,000 hours. However, the use of lasers requires compliance with stringent safety regulations, and require a greater degree of care in operation.

In one embodiment, light source 34 includes a broad-band light source such as an arc lamp or a flash lamp. For measurements in photo-luminescent mode, high pressure arc amps with a broad available excitation wavelength range offer greater output in the blue and UV wavelength range as compared to laser light sources. Arc lamps unfortunately have an output that tends to decay over time, and have a long warm-up time and relatively short life. Exceptions to these are the recently available high-pressure, short arc lamps designed for use in liquid crystal display projectors and similar devices. Flash lamps have the ability to produce more UV light (for photo-luminescence) and also permit intermittent operation, which extends operational life. Flash lamps also do not have warm-up time problems.

For example, light source 34 can include a high-pressure mercury or metal-halide short-arc lamp. The desirable characteristics of these types of lamps include high radiance, long life, and high color temperature. An example of such a lamp is the 100 Watt Phillips UHP lamp, which has a rated lifetime of 10,000 hours, an arc gap of 1.3 millimeters, and a color temperature of around 9,000 degrees Kelvin. Similar lamps are available from Osram, PEC Lamp Corp., and Ushio. Since the light output of these lamps is incoherent, they also avoid problems associated with laser sources when inspecting rough or patterned surfaces, such as speckle and bright diffraction patterns. These lamps also have high output in the low wavelength range (e.g., 400–500 nanometers) which is useful in obtaining high resolution images and in improving detection sensitivity. Furthermore, these lamps also output significant ultraviolet radiation and therefore enable operation in the fluorescent detection mode described in more detail below. For example, light output from a 100 Watt Phillips UHP Lamp is reported to be 25 Watts in the visible band and 6 Watts in the UV band.

Other types of light sources can also be used, such as a commercially available 75–300 Watt xenon arc lamp or a 50–250 Watt quarts tungsten halogen (QTH) lamp, which emits a collimated, one inch or larger diameter circular light beam of uniform intensity.

Referring back to the figure, light source 34 has a light beam port 60 which is optically coupled to an input face of mixer rod 38. In one embodiment, light source 34 includes an integral elliptical reflector to efficiently collect and focus the emitted light. Alternatively, an integral parabolic reflector can be used to generate a collimated beam and then a condenser lens to focus the beam onto a small area. To reduce the transmission of heat into the illumination zone on substrate 33, the integral reflector preferably has a di-chroic cold mirror surface to selectively reflect a visible light component (with a wavelength range of 400–700 nanometers) as opposed to the infra-red (IR) radiation at wavelengths greater than 700 nanometers. A hot mirror surface can be used in the light beam path 37 to further attenuate infra-red radiation to acceptable levels. Cold mirrors 40 and 50 also attenuate IR radiation. One or more fans (not shown) can be used to provide convection cooling and maintain the illumination housing at a controlled temperature.

Mixer rod 38 collects and homogenizes the focused light beam emerging from light source 34. In one embodiment, the cross-section of mixer rod 38 (or clad glass rod) is rectangular. To maximize light beam throughput, mixer rod 38 has an aspect ratio approximately equal to that of the cross-section of the light beam that is projected on to the substrate being inspected. For example, when inspecting a 300 millimeter wafer which is illuminated at a 5 degree angle of incidence to the wafer surface, a mixer rod having a three millimeter thickness, a 33 millimeter width and a 66 millimeter length could be used, with an input face placed at the focal point of the output reflector in lamp 34. Mixer rod 38 can be replaced by alternative optical integrators such as lens arrays (a fly-eye lens) and holographic diffusers.

The light beam emerging from mixer rod 38 is passed to an anamorphic lens assembly through baffle 39, mirror 40 and aperture 42. The anamorphic lens assembly is formed by one or more cylindrical lenses 44, which further shape the light beam traveling along light beam path 37 so that the aspect ratio of the light beam cross-section is substantially close to a desired value. The diverging light beam exiting the anamorphic lens assembly is collimated using a second lens assembly 46. The second lens assembly 46 has a large aperture and can include a Fresnel lens, for example. Fresnel lens 46 can be replaced by other lenses, such as a full-aperture cylindrical lens in alternative embodiments.

In order to prevent stray light from reaching substrate 33, illuminator 14 includes one or more stray light baffles 48. In one embodiment, stray light baffle 48 has a honeycomb structure with optically absorbing surfaces which are aligned with light beam path 37 so as to trap stray light without substantially hindering the passage of collimated light. The light beam exiting stray light baffle 48 is passed to cold mirror 50, which projects the light beam onto an upper surface of substrate 33 through filters 52, 54 and 56 and mask 58. In one embodiment, the light beam illuminates substantially the entire upper surface of substrate 33 and is oriented to form a grazing angle of incidence 62 relative to the upper surface of substrate 33. A grazing angle of incidence is defined as an incidence angle between zero degrees and ten degrees from a vector parallel to the upper surface of substrate 33. The final collimating elements (lens 46 and mirror 50) can be replaced by a parabolic or spherical reflector in alternative embodiments.

Polarizing filter 52 polarizes the light beam, while bandpass filter 54 limits the wavelength range of the illuminating light. A variable density "wedge"0 filter 54 compensates for uneven distribution of incident light on substrate 33. When the substrate to be inspected is circular, such as in the case of a semiconductor wafer, a mask 58 with an elliptical aperture is used to illuminate the wafer. To minimize the deleterious effects of stray light, it is preferred that the illuminating beam be shaped so that only the substrate surface is illuminated. For example, in the case of 300 millimeter semiconductor wafer being illuminated at a 5 degree angle of incidence to the surface, the collimated beam from illuminator 14 can have a cross-section in the shape of an ellipse with dimensions of approximately 300 millimeters by 26 millimeters, corresponding to an aspect ratio of 11.5:1. Illuminator 14 can include various other beam-shaping optics in various arrangements in alternative embodiments of the present invention. The illumination scheme shown in FIG. 1 could also be used in a photoluminescence mode. In this mode, ultraviolet (UV) cold mirrors would be used in place of visible light mirrors 40 and 50.

In addition, the light beam and the light beam path can have various other shapes and angles of incidence relative to substrate 33 in alternative embodiments of the present invention. For example, the light beam can be collimated, non-collimated and can be generated by an active source or a passive source. The term active source refers to a primary light source which actively generates light through an energy conversion process, whereas the term passive light source refers to source which emits light by specular or diffuse reflection. The light beam path can be oriented at a grazing angle or a non-grazing, larger angle of incidence for acquiring images in a brightfield mode, as opposed to a darkfield mode. The light beam path can also be oriented normal to substrate 33. In one embodiment, illuminator 14 is replaced with a conical beam source positioned above substrate 33 an illuminating the entire substrate. Alternatively, a uniformly illuminated white panel can be placed in the background, with camera 22 imaging substrate 33 from an angle not normal to the substrate surface. The camera image includes the substrate pattern superimposed on the reflected white background. This method effectively produces a bright field image free of diffraction.

In the embodiment shown in FIG. 1, as the light beam from light source 34 reflects off of the active surface of substrate 33 particles or other surface defects residing on the active surface scatter light from the light beam path. The scattered light from the active surface is referred to as non-specularly reflected light. The intensity of the scattered light due to a defect is a function of the size of the defect.

Specularly reflected light 70 is trapped by light trap 24. In one embodiment, light trap 24 is contained in a separate compartment than substrate 33. A window 72 transmits the specularly reflected light 70 through enclosure wall 32 to mirror 74, which directs the light toward light trap 24. Light trap 24 has light absorbing surfaces (optical baffles). The inside surfaces 75 surrounding light trap 24 are also provided with light absorbing surfaces to trap stray light from the substrate being inspected.

Camera 22 is supported above substrate 33 and is oriented to acquire images of the non-specularly reflected light that is scattered from particles and other defects and features on the active surface of substrate 33. Camera 22 preferably has a variable exposure to enable the detection to be optimized with respect to particle size and surface conditions. In one embodiment, camera 22 includes a scientific grade, slow-scan, cooled CCD camera, such as a commercially available Photometrics Model Sensys 1400 series camera, which is operated in a high signal-to-noise mode for detection of weak signals on bright backgrounds. Cooled CCD cameras have an active cooling device, such as a thermoelectric cooling device, for cooling the photodetector array. Cooled CCD cameras have lower dark current. Slow-scan CCD cameras have image readout times that are much slower than video cameras, such as 0.1 frames per second to 10 frames per second, depending on the size of the photodetector array. Slow-scan CCD cameras also do not need to operate continuously, and inspection module 10 can therefore acquire snapshot images on command. Slow-scan CCD cameras have low read-out noise. In an alternative embodiment, camera 22 includes a video camera. Conventional video cameras produce images at 30 frames/second, and operate in a continuous mode.

Camera 22 includes a lens 80 and an internal charge-coupled device photodetector array 81. Lens 80 collects a fraction of the light scattered from the active surface of substrate 33 and applies the collected, scattered light to photodetector array 81. Lens 80 can include a commercially available high resolution camera lens for providing adequate light collection for the selected spatial resolution, such as a Navitar model DO-1213 CCTV lens with an aperture of F/1.3 and a focal length of 12.5 mm. Lenses with variable magnification ranges may be used to image differently sized substrates. One or more optional filters 82 can be positioned between lens 80 and the active surface of substrate 33.

Photodetector array 81 defines an image plane 84 for camera 22, which lies within a focal plane of lens 80. The term "focal plane" refers to the surface (plane) on which an image transmitted by lens 80 is brought to sharp focus. Photodetector array 81 is divided into a plurality of pixels, with each pixel corresponding to a unit area on the active surface of substrate 33. The plurality of pixels together have a field of view 86 which covers substantially the entire active surface of substrate 33. A large photodetector array is desired for good spatial resolution. In one embodiment, photodetector array 81 includes an array of 1024 by 1024 pixels, wherein each pixel has an area of 24 $\mu$m by 24 $\mu$m on the photodetector array.

Camera 22 also includes digitizing and computer interfacing circuitry in which the light intensities detected within each pixel of the photodetector array are converted to form a grey level image. The grey level image is coded in a standard format, such as an 8-bit or 16-bit TIFF format, which is provided to output 90. Output 90 can include an 8-bit, 12-bit or 16-bit output, for example. A 12-bit output provides a high definition image with a 4096 grey level image depth. A 16-bit output provides a 65,536 grey level image depth.

In one embodiment, computer controller 26 preferably includes an microprocessor-based workstation having standard communications interfaces 92 and 94. Interface 92 is coupled to output 90 to enable computer controller 26 to communicate with camera 22. Interface 92 can include an RS 232 or an IEEE 488 interface, for example. Interface 94 can include an SECS interface, for example, to enable computer controller 26 to communicate with other computers in a multi-process cluster tool system. The information communicated to the other computers can include inspection status, inspection data, analysis results, a pass/fail signal or test scheduling information for example. Computer controller 26 can also include an interface 96 for controlling light source 34. Additional interfaces can also be included for controlling any transport arms for loading and unloading each substrate 33 into and out of module 10.

Computer controller 26 is provided with software drivers for controlling the operation of camera 22, communicating with other computers and analyzing images acquired by camera 22. All software is stored in a computer-readable medium such as a hard disc drive, a CD-ROM, a floppy disc, or random access memory which is associated with computer controller 26. During inspection, the images acquired by camera 20 are processed by computer controller 26 to identify and count particles and other defects such as scratches, stains, residue, finger prints and pits. Computer controller 26 can be used to control a single inspection module or multiple inspection modules at the same time.

During operation, camera 22 captures images of substrate 33 while the substrate is illuminated by light source 34 at a grazing angle of incidence. These images are analyzed by computer controller 26 to determine the number and location of particles and other defects on the active surface. The presence of particles and other defects and features within each unit area of substrate 33 is identified as a function of the measured intensity within the corresponding pixel in the photodetector array. In one embodiment, the measured intensity, or grey level value, within each pixel is compared with an intensity threshold. This allows light scattering caused by particles to be distinguished from light scattering caused by surface roughness or other background features. Each pixel having a measured intensity that exceeds the intensity threshold corresponds to an area on substrate 33 having a particle or other defect or feature. A list of particle or defect locations on substrate 33 is generated based on the location of each of these pixels relative to the other pixels in photodetector array 81. Multiple intensity threshold levels can also be used.

A count of the total number of particles residing on the active surface of substrate 33 is generated based on a count of the number of pixels having a measured intensity that exceeds the intensity threshold. In one embodiment, groups of these pixels that are spatially contiguous with one another in photodetector array 81 are considered as representing a single defect or feature on the active surface. The shape of the defect or feature can be analyzed to classify the type or source of the defect, such as a particle, a stain, a finger print or a scratch, or the type of feature.

FIG. 2 is histogram illustrating an example of the number of pixels in an image of substrate 33 as a function of grey level value for the case of an unpatterned wafer. Line 110 represents an intensity threshold. Pixels having a grey level value above intensity threshold 110 are activated by light scattered from particles (or other surface features) above a predetermined size. Pixels having a grey level value below intensity threshold 110 are activated by light scattered from particles or surface roughness below the predetermined size. Image enhancement techniques may be used to obtain the highest sensitivity to particles and detects for particular applications.

Referring back to FIG. 1, inspection module 10 can further include an additional brightfield illumination source (not shown) which generates a light beam that is oriented substantially at a non-grazing angle of incidence to the active surface of substrate 33 and illuminates substantially the entire active surface, in an alternative embodiment. Specularly reflected light from the surface of substrate 33 from the brightfield illumination source is then collected by lens 80 and applied to photodetector array 81 within camera 22. The image acquired under brightfield illumination can be analyzed by computer 26 to detect the perimeter and orientation of substrate 33 by using edge detection software, for example.

2. Alternative Illumination Arrangement

FIG. 3 is a schematic representation of a large area optical inspection module 150 according to an alternative embodiment of the present invention. The same references numerals are used in FIG. 3 as were used in FIG. 1 for the same or similar elements. Inspection module 150 is essentially the same as inspection module 10, but includes an alternative illuminator 152.

Illuminator 152 includes a high-pressure short-arc lamp 154 with in integral elliptical reflector, a cold mirror 156, a mixer rod 158, a projector lens 160, a cold mirror 162, stray light baffles 164 and 166, a cold mirror 168, a polarizing filter 52, a band-pass filter 54, a wedge filter 56 and a mask 58. These components are arranged to form a light beam path 170 from arc lamp 154 to the surface of substrate 33 for illuminating substantially the entire area of the substrate at a grazing angle of incidence. Once again, mixer rod 158 is an optical integrator used to collect and homogenize the output of lamp 154, while multiple cold mirrors 156, 162 and 168 are used to "steer" the beam and attenuate the infra-red component of the emitted light.

Projector lens 160 is a "relay" lens that projects an image at the output face of mixer rod 158 onto substrate 33. Projector lens 160 can include a commercially available camera lens, such as an f/2 100 millimeter focal length lens designed for 35 mm format cameras, with an added planoconvex element preceding the lens to provide telecentric light collection. A suitable camera lens can include a six-element double Gauss relay lens, for example. Such telecentric light collection achieves efficient collection of light emerging from mixer rod 158. A spherical mirror (not shown) could be used to collimate the diverging beam if necessary. As in the embodiment shown in FIG. 1, stray light baffles 164 and 166, mask 58 and filters 52, 54 and 56 are placed in light beam path 170 to suitably condition and shape the beam.

3. Measurement of De-Polarized Scattered Light

The optical inspection module shown in FIGS. 1 and 3 can be adapted to measure depolarized light scattered from the substrate surface, which can be advantageously used to inspect patterned wafers having high background scattering levels. Referring back to FIG. 1, filter 82 is replaced with a cross-coupled polarizing filter (analyzer). Polarizing filter 52 in illuminator 14 is placed in the illumination light beam path to linearly polarize the light beam that is incident on the substrate surface. Defects on the substrate surface alter the polarization state of the reflected/scattered light, and are detected with high contrast using cross-coupled polarization filter 82. In one embodiment, the polarization axis of filter 82 is perpendicular to that of polarizing filter 52. Filter 82 transmits the depolarized light from defects, while attenuating the polarized light from the background surface. In one embodiment, polarizing filter 52 illuminates substrate 33 with s-polarized light, while filter 82 enables detection of p-polarized light.

FIGS. 4A–4C show example results obtained by inspecting a patterned wafer through depolarized light with an optical inspection module such as that shown in FIG. 1. While the entire surface of substrate 33 was imaged, FIGS. 4A–4C show only a small portion of the image. In each image, a patterned wafer was illuminated by linearly polarized light. FIG. 4A is an image of the wafer taken without cross-polarized filter 82 in the detection beam path. FIG. 4B is an image of the wafer taken with cross-polarizing filter 82 in the detection beam path. The image shown in FIG. 4C represents the image shown in FIG. 4B after being filtered by a two-stage computerized filtering process to highlight defects with respect to the background. It is seen that the detection of depolarized light (the image shown in FIG. 4B) improves the contrast between defects and background.

4. Measurement of Photo-Luminescent Light

Photo-luminescence measurements, including molecular fluorescence and phosphorescence, have been used for analysis of chemical compounds and other materials. Fluorescence measurements have been used in the semiconductor industry for particle contamination and defect detection, for measurement of critical dimensions, for film thickness measurements, for end-point detection and for etch rate measurements.

The optical inspection modules shown in FIGS. 1 and 3 can be adapted for making photo-luminescence measurements while imaging the entire wafer at one time. These measurements can be used for inspecting semiconductor wafers for the presence of contaminants such as photo-resist residue, skin flakes, fiber from clothes, and flakes of polymeric dielectric materials such as polyimids, etc. Such contaminants emit longer wavelength fluorescent light when irradiated with ultraviolet light (having wavelengths less than 400 nanometers) or with blue or green light (having wavelengths of 400–520 nanometers). For example, module 250 can be used to inspect a wafer for residual photo-resist after an oxygen plasma ashing operation.

For making photo-luminescence measurements, light source 34 can include any light source, such as an arc lamp, that is capable of emitting light in the UV wavelength range. In an alternative embodiment, a "line source" such as a fluorescent tube (e.g., a germicidal lamp) or a linear flash tube fitted with a parabolic reflector is used to produce a beam with a substantially rectangular cross-section. Light source 34 can alternatively include a laser with suitable collimating optics to produce a light sheet with a rectangular cross-section.

Polarizing filter 52 is removed, and band-pass filter 54 is adapted to transmit excitation light within a selected wavelength range (such as in the range 250–500 nanometers), that contains wavelengths known to excite fluorescence from a broad range of organic materials including for example, specific photo-resists. The incident UV light excites fluorescent emission in the visible wavelength range from selected organic compounds on the wafer surface, and a portion of the emitted light is collected by camera 22. Specifically, these organic compounds absorb energy from the excitation light and emit photons of lower energy in a different wavelength range than the excitation light.

To distinguish the fluorescent light emission from scattered light, filter 82 is replaced with a long pass filter, which blocks substantially all non-fluorescent light. In one embodiment, long pass filter 82 has a cut-on frequency above 500 nanometers. If a laser light source is used, long pass filter 82 may be replaced by a holographic notch filter to reject the scattered laser light and transmit only the fluorescent light. For flexibility, inspection module 10 may also be provided with multiple sets of excitation and emission filters optimized for fluorescence measurements with specific target materials. Such filter sets may be obtained commercially, for example from Spindler and Hoyer, Inc. of Milford, Mass.

To prevent stray light or artifacts from influencing camera 22, enclosure 12 preferably has non-fluorescing surfaces, and is constructed using components made of non-fluorescing materials. Since the background fluorescence emission is then essentially zero, this technique provides a very sensitive technique for detecting organic contaminants on the surface of the substrate being inspected, with the entire wafer surface being imaged at one time.

In one embodiment, a variety of different types of filters 52, 54 and 82 are physically moved into and out of the illumination and detection paths to switch between a variety of different modes of operation. For example, module 10 can be operated to detect i) unpolarized light scattering; ii) cross-polarized light scattering; and iii) flourescence. The filters can be moved manually by an operator or automatically under the control of process controller 26. Also, one or more images can be taken in each operating mode and can be later combined or compared by software to enhance detection or analysis.

5. Operation in Off-Axis (Scheimpflug) Imaging Mode

In the embodiments discussed above, the optical axis of the camera lens is normal to the image plane of the camera, and also to the object plane on the substrate surface. In an alternative embodiment, the camera is arranged in a Scheimpflug imaging mode, where the camera lens axis is not normal to the substrate plane. Rather, the lens axis is oriented at an oblique angle to the substrate surface. In this configuration, the entire substrate can be illuminated at any angle of incidence to the substrate, and the incident light beam can be collimated or not collimated. Also, the illumination source can be passive or active. The camera lens can be positioned relative to the substrate to collect forward scattered light, backward scattered light, or side scattered light while avoiding the specularly reflected light.

FIG. 5A schematically illustrates a simplified optical inspection module 260 which is configured for detection of an active surface 272 of a substrate 270 at an oblique angle. Substrate surface 272 defines an object plane 274. Module 260 includes a camera 276, a lens 278 and additional components such as those shown and discussed with respect to the previous figures for illuminating substrate surface 272 and imaging light scattered from the surface.

Camera 276 has an image plane 280 which is not parallel to object plane 274 as in the previous figures. In the embodiment shown in FIG. 5A, image plane 280 is substantially perpendicular to object plane 274. Other angles can be used in alternative embodiments. Lens 278 has an optical axis 279, which is oriented at an oblique angle 281 relative to object plane 274. As a result, lens plane 282 is not parallel to object plane 274. lens plane 282 is tilted relative to image plane 280 so that the entire substrate surface 272 remains in focus on image plane 280. This allows the use of a wide aperture imaging lens with high light collecting ability despite having a small depth of field. In this configuration, object plane 274, image plane 280 and lens plane 282 all intersect along a line going into the page in FIG. 5A, at point 284. Oblique angle 281 can be any oblique angle, such as 40–45 degrees from the substrate surface. In one embodiment, the illuminating light beam (not shown in FIG. 5A) is oriented at a grazing angle of incidence relative to substrate surface 272.

FIG. 5B is a simplified schematic illustration of module 260 as viewed from a direction normal to substrate surface 272, which defines the object plane 274. Arrow 285 schematically represents the illuminating light beam and its directional component in object plane 274. Camera 276 and lens 278 are oriented at an angle relative to the directional component of light beam 285 within object plane 274. The optical axis 279 of lens 278 is oriented at a non-zero azimuthal angle 286 to the directional component of light beam 285 relative to object plane 274. When module 260 is configured in a "dark-field" imaging mode, any azimuthal angle 286 can be used as long as lens 278 avoids collection of specularly reflected light. The azimuthal angle 286 can be set to collect forward scattered light (less than +/−90 degrees), backward scattered light(greater than +/−90 degrees), or side scattered light (at about 90 degrees) while avoiding the specularly reflected light.

Example configurations for inspecting 200 millimeter and 300 millimeter diameter semiconductor wafers using the off-axis Scheimpflug imaging mode shown in FIGS. 5A and 5B are given below in Table 1.

TABLE 1

| Wafer Size, mm | Camera or CCD chip | CCD chip Resolution | Lens Focal Length and Aperture | Nominal Magnification | Working Distance | Angle From Normal |
|---|---|---|---|---|---|---|
| 200 | Sensys 1400 | 1315 × 1035 | Navitar 12.5 mm F1.3 | 1/23 | 30 cm | 50° |
| 200 | Sensys 1600 | 1536 × 1024 | Navitar 12.5 mm F1.3 | 1/16.7 | 30 cm | 45° |
| 300 | Sensys 1600 | 1536 × 1024 | Navitar 12.5 mm F1.3 | 1/25 | 32.5 cm | 40° |
| 300 | Kodak KAF-6300 | 3072 × 2048 | Nikkor 28 mm F1.4 | 1/12 | 36.5 cm | 40° |

Off-axis imaging enables higher sensitivity when inspecting microelectronic substrates with high levels of background scattering. Such a configuration can also be used in an integrated metrology system when optical access to the substrate is only possible from an oblique view such as from a window on the side wall of a process chamber. In the case of rectangular format imaging detectors, it enables a greater fraction of the detector surface area to be used for imaging the active surface of the substrate. It should be noted that the image shape is distorted when operating in this imaging mode, and coordinate transformations should be used to map defects accurately.

The off-axis imaging configuration shown in FIGS. 5A and 5B enables better signal-to-noise performance analogous to that achieved by so called "double-dark field" detection configurations used in prior art laser wafer scanners. In these scanners, a small laser spot is raster scanned across the wafer surface. A single photodetector detects the scattered light at an oblique angle. These scanners are not capable of imaging the entire active surface at one time. Rather, only a small portion of the wafer is illuminated at a time, therefore requiring the wafer to move relative to the illuminator beam to enable the entire surface to be inspected. In the embodiment shown in FIGS. 5A and 5B, the entire active surface is imaged at one time, with the entire active surface remaining in focus on the image plane 280. This provides a significant increase in efficiency and sensitivity of the inspection module.

In an alternative embodiment of the present invention, lens axis 279 (shown in FIG. 5A) is oriented at an oblique imaging angle relative substrate surface 272 while the substrate is illuminated at a relatively large angle of incidence, such as substantially normal to the substrate surface. For example, substrate surface 272 can be illuminated from above (at any angle) with a conical beam eminating from a point source while imaging in an off-axis mode to avoid specular reflection into camera 276.

In another alternative embodiment, shown schematically in FIG. 5C, inspection module 260 includes a uniformly illuminated white panel 288, which is placed to the side of substrate, opposite to lens 278. Lens 278 and camera 276 image substrate 270 from an angle not normal to the substrate surface. In this example, panel 288 is oriented perpendicular to substrate surface 272 and emits diffuse light 289 that illuminates the entire substrate surface 272. The image acquired by camera 276 includes the substrate pattern superimposed on the reflected white background from panel 288. This method effectively produces a bright field image free of diffraction from substrate surface 272.

In yet another alternative embodiment shown in FIG. 5D, optical inspection module 260 includes a plurality of detectors, wherein each detector has an optical lens axis that is not perpendicular to the object plane. The same reference numerals are used in FIG. 5D as were used in FIG. 5A for the same or similar elements. Module 260 has an additional CCD camera 290 having an image plane 292 and an additional lens 294 having a lens plane 296 which is tilted relative to image plane 292. Image plane 292, lens plane 296 and object plane 274 intersect along a line going into the page in FIG. 5D at point 298. Lens 294 has an optical axis 297 which is oriented at an oblique angle relative to substrate surface 272. The optical axis 297 of lens 294 is also oriented at a non-zero azimuthal angle to the directional component of the illuminating light beam relative to object plane 274, similar to that shown in FIG. 5B for camera 276 but at a different azimuthal angle. This angle can be set to collect forward scattered light, backward scattered light, or side scattered light while avoiding the specularly reflected light. In an alternative embodiment, the second camera 290 and lens 294 are positioned on-axis, above substrate 270, similar to camera 22 and lens 80 shown in FIG. 1.

The use of two or more detectors allows the entire active surface of substrate 270 to be imaged at one time from two or more different angles. The plurality of images can then be used to further enhance the detection software. One advantage of acquiring images at different angles is that the images may allow for differentiation between scratches and pits from surface defects. Another advantage is that scratches might show up in the acquired image in one imaging direction but not in another due to the directionality of the scattering signal. Also, the diffraction hot spot problem discussed below with respect to inspection of patterned wafers can be solved by imaging the wafer at several different angles. Regardless of the detector setup, each imaging angle produces a unique view of the surface for patterned wafers. The good image data from the images acquired from the different angles can then be stitched together in software to form a combined image that is free of diffraction hot spots caused by the background wafer pattern. In addition, to cameras 276 and 290, a further camera such as those shown in FIGS. 1 and 3 can be used, which have an image plane and a lens plane that are parallel to the object plane. The use of two or more images at different angles also enables improved false defect count rejection and on-the-fly defect characterization by using combinations or comparisons of the multiple images.

In yet another alternative embodiment, one or more off-axis detectors such as those shown in FIGS. 5A–5D can be used while rotating substrate 270 about an axis 299 relative to the light beam path and the detectors. As substrate 270 is rotated about axis 299, images are collected from the camera (or cameras) at each substrate position. This can further enhance the ability of the inspection module to detect light scattered from particles and other defects on the substrate surface relative to background scattering an can enhance the ability to classify the defects. In addition, rotation of substrate 270 can be used to achieve a desired substrate orientation. For example, an image of substrate 270 can be taken (on-axis or off-axis) to measure its rotational orientation. Substrate 270 is then rotated to the desired orientation and another image (on-axis or off-axis) is taken for defect measurement and detection.

Alternatively, substrate 270 can remain fixed and the position of the camera (or cameras) can rotate about axis 299. As the camera (or cameras) is rotated about axis 299, images are collected from the camera (or cameras) at each camera position. This has the additional effect of moving the detection angle relative to the direction of illumination.

6. In-Line Wafer Inspection

In addition to the use of the optical inspection module as a stand alone wafer inspection tool, the high throughput and compact footprint of the module make it ideal for use as an in-line wafer inspection device for cluster tools. U.S. Pat. No. 5,909,276 to Kinney et al. discloses a wafer inspection module which is integrated as one of several processing modules in a multi-process "cluster tool" system. A cluster tool is a manufacturing system that includes a set of environmentally isolated process chambers or modules which are linked by a material handling interface and a computer communications interface. The material handling interface transports a workpiece between the various modules in the system. The computer communications interface controls the sequential steps. Clustering multiple operations within a single manufacturing system leads to benefits such as increased process yield (due to less wafer handling and improved process control) and reduced process cycle time. There are several types of clustering systems, such as vacuum cluster tools for deposition and etching, lithography tools, chemical-mechanical polishing systems, and ion implant tools, etc. While each of these tools may have widely differing arrangements, they are collectively referred to as "cluster tools" within the present specification and claims.

Integrating an inspection module as one of several processing modules in a cluster tool system could require different mechanical, electrical, computer communications and software interfaces for each unique cluster tool system. The customization associated with such an integration approach increases developed costs when integrating the module into a wide range of cluster tools made by different original equipment manufacturing (OEM) vendors.

In one embodiment of the present invention, these difficulties are avoided by integrating the inspection module at the wafer load/unload port of the cluster tool. The semiconductor equipment industry, for example, has evolved standard wafer loading/unloading modules which are commonly used by most OEM vendors in their equipment. One example of such a standard is the "front-end" wafer handling systems based on the SEMI standard front opening unified pod (FOUP) carrier for 300 millimeter wafers. Another example is the standard mechanical interface (SMIF) system.

FIG. 6 is a schematic illustration of a multi-process cluster tool system 300 in which an inspection module 302 has been integrated. Cluster tool system 300 includes a wafer loading/unloading module 304 with load/unload ports 305 and 306. In one embodiment, inspection module 302 is "docked" at load/unload port 305, and a standard front opening unified pod (FOUP) 308 is "docked" at load/unload port 306. Pod 308 holds a plurality of wafers in horizontally oriented slots to be loaded into or unloaded out of cluster tool system 300. Wafer loading/unloading module 304 includes a wafer handling robot for transporting individual wafers to and from ports 305 and 306 and load lock chambers 310 and 312 of cluster tool system 300.

Cluster tool system 300 further includes a plurality of substrate processing stations 314–317. Each process station 314–317 has a process chamber entrance 318 for providing access to the respective process station. A common material transport arm 320 interfaces with load lock chambers 310 and 312 and process stations 314–317 along a predefined substrate travel path. In FIG. 6, transport arm 320 is shown transporting a substrate 322 into process station 316. Cluster tool controller 324 controls cluster tool system 300 and its transport arm 320. Controller 324 also controls the wafer handling robot within module 304 and communicates with optical inspection module 302 to schedule an inspection step in the overall process sequence determined by controller 324.

Inspection module 302 has an entrance 330 through its enclosure which communicates with wafer load/unload port 305 to allow access by the wafer handling robot within module 304. For example, entrance 330 is configured consistently with a standard wafer mechanical and electrical handling interface, such as the FOUP or the SMIF interfaces. Since inspection module 302 holds only a single wafer at the inspection position at a time, module 302 is configured to appear to the wafer handling robot within module 304 as having only a single empty "slot" into which the wafer to be inspected may be placed. Other equivalent approaches could also be used in integrating an optical inspection module into a wafer load/unload system. One general approach is to integrate the optical inspection module as a dedicated wafer inspection station into a wafer load/unload port as shown in FIG. 6.

FIG. 7 is a schematic illustration of inspection module 300, which shows the insertion of substrate 322 by the wafer handling robot of wafer load/unload module 304 shown in FIG. 6. Inspection module 300 includes enclosure 350, illuminator 352, illumination light beam path 354, light trap 356, detector 358 and computer controller 360. Wafer handling robot arm 362 has a retracted position 364 (shown in phantom) relative to inspection module 300 in which substrate 322 is positioned external to enclosure 350. Robot arm 362 has an extended position 366 in which substrate 322 is positioned internal to enclosure 350. In extended position 366, robot arm 362 extends through entrance 330 and supports substrate 322 at a predetermined substrate holding position relative to light beam path 354 and detector 358 during the inspection process. A separate holder, such as holder 20 shown in FIG. 1 can be used in alternative embodiments. The substrate holding position is viewed by robot arm 362 as a single empty "slot" into which substrate 322 may be placed. As in the previous embodiments, illuminating light beam path 354 illuminates substantially the entire active surface of substrate 322 at a grazing or non-grazing angle of incidence. Detector 358 has a field of view which is capable of imaging substantially the entire active surface of substrate 322 at one time. Detector 358 can have an optical axis that is either normal to the substrate surface or at an oblique angle relative to the substrate surface.

7. Inspection Module with Multi-Measurement Function

When processing semiconductor wafers and similar micro-electronic substrates, it is often useful to monitor more than one variable relating to the substrate being processed. For example, during a chemical vapor deposition (CVD) process for depositing a thin film of dielectric or metal on a semiconductor wafer, it may be advantageous to monitor film parameters such as thickness, refractive index, resistivity and stress, in addition to the number of particles on the wafer being processed. In integrated metrology applications, since the available area within a cluster tool is limited, it is advantageous to provide a capability for multiple integrated metrology within a single compact platform. The platform can be configured as a stand-alone system or as one of the processing stations in a cluster tool such as that shown in FIG. 6.

FIG. 8 is a schematic illustration of an integrated metrology station 400 according to one embodiment of the present invention. Similar to the previous embodiments, station 400 includes an enclosure 402, a light source and beam shaping objects 404, an illumination light beam path 406, a substrate holder 408, a large array, cooled CCD camera 410, a light trap 412 and a computer controller 414. Illumination light beam path 406 illuminates substantially the entire surface of a wafer 416 at one time, and camera 410 has a field of view 418 which is capable of imaging the substantially the entire surface of substrate 416 at one time.

In addition, station 400 includes a second instrument 420, such as a film metrology head or microscope, which enables measurement station 400 one or more measurements in addition to defect detection, such as detect review and film property measurements. Film metrology head or microscope 420 is mounted on an X-Y (or r-θ) stage 422, for example, which positions the sensor over the substrate 416 being measured. Station 400 is preferably provided with a transparent window (not shown) placed over substrate 416 to protect the substrate from particle contamination generated by motion of the X-Y stage 422. When the film metrology head or microscope 420 is not being used, it can be positioned out of the field of view 418 of camera 410. This configuration permits both defect detection and film property measurements to be independently performed. In one embodiment, the film metrology head or microscope 420 measures film properties using a spectral reflectance technique. The film metrology head can also incorporate a microscope, so that it can be used for defect review and mapping in addition to film property measurements.

8. Digital Image Analysis for Defect Detection

The digital images acquired by the detection cameras shown in the above-embodiments are collected and analyzed by the associated computer controller during inspection of each substrate. Each image is a record of the intensity of scattered light arriving at the camera from different points on the substrate surface. Defects are extracted from the scattered light images through image analysis techniques.

Various analysis techniques can be used to process the images. In one embodiment of the present invention, a pixel-to-pixel comparison is made between the test image and a known good reference image stored in computer memory. Those pixels with intensity "difference" values outside a local variance or tolerance range are flagged. The tolerance range accounts for substrate-to-substrate variation, and temporal variation in illumination intensity and camera response, and represents the allowable signal spread for "good parts". The tolerance range may vary in a non-uniform manner over the substrate image, for example, due to variation in illumination intensity and lens resolution over the entire substrate surface and/or due to varying pattern signatures in patterned wafers. For convenience, the pre-computed tolerance range may be stored in memory as a variance image. This variance image can include the individual tolerance range for each pixel in the image. For grey-scale comparison, typically one reference image and one variance image is associated with each different type of substrate being inspected. Different substrate types are classified as those having a surface with either a different film, a different pattern, or a similar pattern at a different processing stage or level. For color images, it may be convenient to breakdown the images into their color components resulting in multiple reference/variance images being used during the comparison process.

FIG. 9 is a flow chart which shows the basic image acquisition and analysis process 450 used to extract defects with the use of a previously stored reference image, according to one embodiment of the present invention. The process shown in FIG. 9 can be implemented through programmed software instructions by the computer controller associated with the inspection module. The computer controller can include dedicated image processing hardware, such as pipeline processors. The programmed software instructions can be stored on any computer readable medium, either internal or external to the controller.

In process 450, a test image of the substrate is acquired by the camera according to any one of the embodiments discussed above, at step 451. At step 452, the test image is normalized to compensate for changes in illumination conditions. Normalizing the test image with respect to a reference image can be accomplished through techniques such as histogram matching and normalizing mean intensities. At step 453, the normalized test image is optionally equalized by performing a gamma correction (a histogram equalization) to enhance the contrast level of the normalized test image. At step 454, the equalized test image is shifted to align it with a previously stored background reference image 455. This shifting can be based on a detected perimeter of the substrate within the test image and any reference features on the substrate. For example, substrates often include a notch on its perimeter for orientation purposes. These features are aligned with corresponding features in the stored background reference image 455. At step 456, the background reference image 455 is subtracted from the test image to produce a difference image.

At step 457, the difference image is compared with a variance image 458 to create an error image that highlights those pixels that are outside the predefined threshold tolerance range. This comparison is done by performing a binary threshold operation on each pixel in the difference image with the threshold value of the corresponding pixel in the variance image. Alternatively, a common threshold value can be used for all pixels. At step 459, a blob analysis is performed on the error image to count and quantify potential defects. At step 460, actual defects are screened, identified and classified from the error image.

In the above process, the shifting and alignment step 454 is particularly important for patterned substrate inspection, where it is needed to compensate for variations in pattern position from substrate-to-substrate. to-substrate. Also, slight variations in the substrate placement position can occur whenever a substrate is placed within the camera field of view by the transport arm. A small subset of pattern features (fiducial marks) may be used for pattern matching on a global scale for the entire substrate. If the pattern has been produced using a step and repeat lithography process, it may be necessary to independently align individual die in the test image with its corresponding counterpart in the reference image to account for random position alignment errors during the lithography process, as well as distortion errors caused by imaging with imperfect optics. This local alignment at the individual die scale may be performed by dividing the test image into unit cells centered around each repeating die, performing the comparison at a unit cell level and the stitching together the unit cells again to obtain the global scale difference image at step 456.

Sub-pixel accuracy in image alignment/registration at both global and local levels is important during image subtraction step 456 to avoid "ghost" differences. For unpatterned wafers, the image alignment may be performed using only global features such as the wafer edge and notch as reference features. For the case of patterned wafers, sophisticated pattern matching techniques can be used to ensure good alignment and registration of patterns to sub-pixel levels. The most powerful techniques have the capability to handle variation in contrast changes, rotation, scale and partially degraded and occluded patterns. Less robust techniques based on normalized grey-scale correlation may also be used under well-controlled conditions.

FIGS. 10A–10D show an example of defects detected using the process shown in FIG. 9 for the case of a patterned wafer. For convenience, only a narrow strip of the wafer is shown in each figure, even though the process is applicable to images covering the entire wafer surface. FIG. 10A shows the stored background reference image. FIG. 10B shows the test image acquired at step 451. FIG. 10C shows the difference image produced at step 456 by subtracting the reference image from the test image. FIG. 10D shows the thresholded image (error image) produced at step 457 by comparing the difference image with the variance image 458. The defects exposed in FIG. 10D can be further analyzed for classification and reporting, at steps 459–460.

9. Image Analysis for Unpatterned Substrate Inspection

The optical inspection module of the present invention can also be used to extract point defects from the image of an unpatterned substrate when it is impractical to use a previously created background reference image. This situation may arise when inspecting blank wafers or the wafer back side surface for contamination, for example. The surface finish on the wafer back side may vary greatly from wafer to wafer and it can become impractical to create the representative background reference image suitable for background subtraction. Nevertheless it is desirable to perform some sort of background correction on the test image in order to account for effects such as non-uniform illumination and thereby permit defects to be separated from the background by using morphological operations such as intensity thresholding. When a background reference image is not available, it is reasonable to use neighborhood pixel information in the test image itself to create a self-reference image for use in background correction.

A convenient way of creating a self-reference image is to apply a convolution filter such as a Laplacian filter to the test image. Application of such a filter is equivalent to subtracting the intensity at each pixel with a neighborhood average intensity background. Convolution filters process images by multiplying the pixel intensity values in a given portion of the image or "image neighborhood" by a matrix of filtering coefficients. This matrix of integer value elements is called a "kernel", and is the same size as the neighborhood to which the kernel is being applied. The results of this multiplication (i.e. of the pixel intensity with the corresponding kernel element) for the neighborhood are summed and divided by the sum of the filter kernel. The result replaces the center pixel in the image neighborhood. Each pixel in an image can be process in this manner. Suitable convolution filters are described in more detail in J. C. Russ, "The Image Processing Handbook", CRC Press, Ann Arbor, Mich. (1995).

The convolution filter has the property of highlighting point and line defects. Other filters with similar properties can be used for this purpose in alternative embodiments of the present invention. In one embodiment of the present invention, this filtering procedure is implemented through computer software operated by the process controller associated with the inspection module.

FIG. 11 is flow chart illustrating an example of a process 480 for implementing spatial filtering with a convolution filter. In process 480, a test image of the substrate is acquired at step 481 with any one of the inspection modules discussed above. At step 482, a Laplacian filter is applied to the test image to accentuate the bright spots, edges or areas typically caused by defects. At step 483, each pixel of the filtered test image is compared to a threshold value 484 (a common value or a value unique to that pixel) to separate pixels having intensities above the threshold value from the background. At step 485, a blob analysis is performed on the separated pixels to count and characterize defect like features. At step 486, a defect geometry selection algorithm is used to screen out "false" defects and report the actual defects found.

FIGS. 12A–12C show a sequence of images where a spatial filtering technique was used to highlight 0.5 micrometer polystyrene latex particles on a virgin 200 millimeter silicon wafer. Again, FIGS. 12A–12C show only a part of the wafer image. FIG. 12A shows the test image acquired at step 481. FIG. 12B shows the Laplacian filtered image produced at step 482. FIG. 12C shows the thresholded image produced at step 483. In this sequence of images, a Laplacian filter was used to separate pixels representing particles from background pixels representing the unblemished surface of the wafer.

The self-referenced method shown in FIG. 11 can also be applied to the inspection of other unpatterned substrates such as magnetic recording discs, flat panels, polished ceramic packaging substrates, etc. It should be understood that the process shown in FIG. 11 is exemplary, and alternative methods can be devised having a similar overall effect. This overall effect is to highlight defect information by performing a self-referencing background correction using neighborhood information.

In one embodiment, the process shown in FIG. 11 is used to create a self-referenced image for the back side of a semiconductor wafer. In order to obtain an image of the back side, the substrate can be physically inverted or "flipped" by the transport arm onto its front side so as to expose the back side to the camera. Alternatively, the substrate holder (such as holder 20 shown in FIG. 1) can be configured to hold the substrate along its perimeter or side edges and a second camera can be positioned to image the back side of the substrate from below the substrate holder, opposite to the first camera. Images of the front and back sides can be taken simultaneously or in sequence with one another.

10. Patterned Wafer Inspection Using Image Analysis Based on Spatial Filtering

The inspection module of the present invention can also be used in a self-reference method for extracting point defects from the image of a patterned substrate, when a previously created background reference image is not available. This situation may arise when using the inspection module to inspect a new type of wafer introduced into the production line for the first time, for example. Aside from this, the self-reference technique can be desirable due to the following advantages. First, there is no need for a reference image data base. Second, there is no need for prior knowledge about the wafer being inspected. Third, there is no need for precise wafer alignment with respect to the illumination source. Fourth, alignment and registration between the test and reference images during background correction is greatly simplified. The self-reference technique described here produces a substantially defect-free reference image from a test image of the wafer being inspected by the optical inspection module. This same technique is also applicable to inspection of unpatterned wafers.

The method is based on creating a defect-free reference image by applying a median filter (or other similar mathematical function such as an average or mean, etc.) to the test image. A median filter has the effect of replacing the intensity of a pixel by the neighborhood median intensity, as described in J. C. Russ, *The Image Processing Handbook*, CRC Press, Inc. (1995). For each pixel in the test image, a corresponding pixel is produced in a reference image, which has having an intensity equal to the mathematical median of the intensities of a selected set of pixels in the test image that surround that pixel. In the present embodiment, the median filter erases point defects from the test image to create a defect-free reference image that is already perfectly aligned with the test image. Performing the image subtraction results in a difference image in which point defects can easily be distinguished. The method is implemented through the computer software used to operate the wafer inspection module or as a subsequent processing step, as discussed above.

FIG. 13 is a flow chart illustrating a spatial filtering process 500 according to one embodiment of the present invention that can be used for processing patterned and unpatterned wafers. A test image of the substrate is acquired at step 501. At step 502, a median filter is applied to the test image to create a reference image in which the bright sharp spots and edges typically caused by defects are attenuated or blurred. At step 503, the reference image produced at step 502 is subtracted from the test image acquired at step 501 to create a "difference" image. At step 504, each pixel in the difference image is compared to a threshold value (or selected variance range) to separate those pixels having intensities above the chosen value (or outside the selected variance range) from the background. Alternatively, a variance image can be used instead of a single threshold value or variance range. At step 506, a blob analysis is performed on the separated pixels to count and characterize defect-like features. At step 507, a defect geometry selection algorithm is used to screen out "false" counts and to prepare a report of the defects found.

It should be understood that the flow chart shown in FIG. 13 is exemplary, and alternative methods can be devised for performing a self-referencing background correction, and using filtering to create a clean reference image from the test image itself.

FIGS. 14A–14D show a sequence of images where spatial filtering has been used according to the process shown in FIG. 13 to detect particles on a 150 millimeter patterned silicon wafer. In FIGS. 14A–14D, only part of the image is shown. FIG. 14A shows the test image acquired at step 501. FIG. 14B shows the median filtered image (reference image) produced at step 502. FIG. 14C shows the difference image produced at step 503. FIG. 14D shows the thresholded image (error image) produced at step 504. By subtracting the reference image in FIG. 14B from the test image in FIG. 14A, bright pixels representing particles can be distinguished from darker background pixels representing the patterned surface of the wafer. The self-reference method described above can also be applied to the inspection of other patterned substrates such as flat panels and ceramic packaging substrates.

11. Patterned Wafer Inspection Using Computer Pattern Filtering (Frequency Filtering)

Optical inspection of patterned wafers is often complicated by the strong localized scattering from the pattern of elements on the integrated circuit being fabricated. The pattern behaves like a diffraction grating and projects a strong diffraction pattern against which the faint scattering signal from a random defect can be difficult to distinguish. Patterned wafer inspection systems of the prior art have used optical components to perform Fourier filtering to selectively attenuate the background pattern. Prior art inspection tools generally have imaged the wafer at a high magnification so that only a small portion of a single die is within the field of view of the system. For such systems, it is important that the pattern on the wafer being inspected has a high degree of intra-die periodicity, such as in dynamic random access memory (DRAM) devices. In contrast, the optical inspection module of the present invention images the entire wafer at one time.

FIG. 15 is schematic representation of a typical patterned wafer 520 showing the regular placement of individual die 522. Lx and Ly are the inter-die pitch spacing in the X and Y directions, respectively. As shown in FIG. 15, a typical patterned wafer has a high degree of periodicity. Each point on a die, whether DRAM or logic, is repeated multiple times in both the X and Y directions. The optical inspection module of the present invention can exploit this periodicity to detect particles and defects on patterned wafers through computer pattern filtering, with no need for a previously created reference image of the patterned wafer.

FIG. 16 is flow chart illustrating a process 530 for computerized pattern filtering to detect defects on patterned wafers. At step 531, the optical inspection module acquires a test image of the patterned wafer. For compatibility with the FFT algorithm used in step 532, the test image preferably has a resolution of $2^m \times 2^n$, where m and n are integers. At step 532, the computer controller (or a subsequent processing computer) applies a fast Fourier transform (FFT) to the test image to create a transform image. The transform image is filtered, such as by using a high-pass filter, at step 533 to remove bright spots corresponding to the pattern on the wafer. The transform image expresses the test image's frequency domain as a symmetrically centered cloud of points, where brightness represents the amplitude of the waveform, and position represents the frequency of the waveform. Regular, periodic features in the test image are mapped onto bright spots in the frequency domain. These "hot" spots with frequencies representing the periodic background are attenuated using a suitable high-pass filter or masking filter. Alternatively, more sophisticated filtering techniques can be used at step 533 to remove features produced by the repeating patterns of die.

The filtered transform image produced at step 533 is then subjected to an inverse FFT transform, at step 534, to recreate an image of the substrate with the background filtered out. At step 535, each pixel in the recreated image is compared to a threshold value 536, which can be a single value, a variance range or corresponding value of a pixel in a variance image. This binary threshold operation separates pixels in the recreated image having intensities above the chosen value from the background. At step 537, a blob analysis is performed on the separated pixels to count and characterize defect-like features. At step 538, a defect geometry selection algorithm is used to screen out "false" counts and to prepare a report of the defects found.

FIG. 17A shows a test image of a patterned 200 millimeter wafer. FIG. 17B shows the corresponding frequency spectrum image obtained by computing the FFT at step 532 in FIG. 16. The simple nature of the frequency spectrum makes it easy to filter. The test image shown in FIG. 17A can be formed using incoherent light, unlike in the case of most prior art systems where coherent light is needed to accomplish the filtering through optical hardware components.

Computer pattern filtering is often computationally intensive. Therefore, this type of filtering is unsuitable for use in prior art wafer inspection systems where a large number of images are needed to inspect a wafer. In contrast, the computer pattern filtering described in FIG. 16 is ideally suited for the optical inspection modules discussed above since only a single test image is processed per inspected wafer. FFT operations can be performed with a 1K×1K resolution image in a matter of seconds.

FIGS. 18A–18E show a sequence of images where computer pattern filtering has been used to detect particles on a 150 millimeter patterned wafer according to the method shown in FIG. 16. FIGS. 18A–18E show only a narrow slice of the wafer image. FIG. 18A shows the test image obtained at step 531. FIG. 18B shows the FFT transform image produced at step 532. FIG. 18C shows the high-pass filtered FFT transform image produced at step 533. FIG. 18D shows the inverse FFT image produced at step 534. FIG. 18E shows the thresholded image (error image) produced at step 535.

12. Wafer Inspection Method Using a Combination of Image Analysis Methods

Three methods for detecting particles on patterned wafers have been described in the preceding sections. The advantages and disadvantages of these three methods are summarized in Table 2 below.

TABLE 2

| | REFERENCE IMAGE SUBTRACTION | MEDIAN FILTERING | FREQUENCY FILTERING |
|---|---|---|---|
| Stored Reference Images | Needed | Not needed | Not needed |
| Pattern Alignment & Registration | Needed | Not needed | Not needed |
| Defect Detection Capability | Most powerful, can detect point, line and area defects | Best for point defects | Periodic defects not detected |
| Periodicity of pattern | Effective for periodic and non-periodic patterns | Effective for periodic and non-periodic patterns | Effective for periodic and non-periodic patterns |
| Wafer Orientation | Prefer fixed orientation | Not fixed | Not fixed |
| Sensitivity | Best | Good | Moderate |

In many circumstances, it may be preferable to use only one of these three methods. However, it has been observed that different inspection techniques have varying degrees of effectiveness for different types of defects. One embodiment of the present invention therefore uses a suitable combination of the multiple image analysis methods for maximizing flexibility of patterned (or unpatterned) wafer inspection.

FIG. 19 is flow chart which shows an example process 550 for combining results from two or more of analysis methods such as those described in Table 3. In one embodiment of the present invention, each of the three methods shown in Table 3 produces a defect map having a plurality of pixels. Each pixel in the defect map comprises a binary value (or other value such as an intensity) indicating whether a defect exists within a corresponding unit area on the substrate surface. The defect maps from each method are input to process 550 at steps 551, 552 and 553, respectively. Suitable masks 554–556 can be applied to defect maps 551–553, respectively, to exclude areas such as the wafer edges, etc. Also, masks 554–556 can be used to negate defects detected within certain areas on the substrate surface for purposes of false count rejection. For example, masks 554–556 can have a plurality of pixels representing a mask image, wherein each pixel has a binary masking value that can vary from one set of pixels to the next according to type and location of features on the substrate imaged by those pixels.

The masked images are then combined by an image operation at step 557. The image operation can include a logical "AND", a logical "OR" or some weighted combinatory operation, for example. A logical "AND" operation can be use to create a conservative defect data set where the number of "false positives" is minimized. With the logical "AND" operation, only those pixels in which all three defect maps indicate the presence of a defect are identified as an actual defect. A logical "OR" operation can be used when it is desirable to maximize the defect detection rate. With a logical "OR", a given pixel is identified as containing a defect if the defect map produced by any one of the three methods indicates the presence of a defect in that pixel. A weighted combinatory operation would give defects identified by one method greater weight relative to defects identified by another operation. The combined image produced a step 557 is then reviewed by the software program for defect detection and classification at step 558.

13. Detection of Defects on Substrates with Noisy Backgrounds

One of the problems associated with the inspection of patterned wafers is the high dynamic range of the background scattering that arises from the integrated circuit patterns etched on the wafer surface. When the optical inspection module of the present invention is used to inspect patterned wafers, the patterns act as diffraction gratings and the intense, highly directional scattering results in test images having a highly non-uniform intensity background. For images possessing such a high dynamic range in intensity, the bright regions limit defect sensitivity by limiting the allowable range of camera integration (exposure) times for which pixels are not saturated. When a pixel is saturated, no information on the presence or absence of defects can be obtained. In such as situation, one method to avoid a decrease in sensitivity is to maintain the long exposure times while masking out the saturated regions of the test image prior to performing the image analysis steps. This masking can be implemented through the software programs associated with the computer controller.

Diffraction from patterned wafers is highly sensitive to wafer orientation with respect to the incident light beam. One way to inspect the entire wafer surface are is to acquire multiple test images with the same wafer oriented at different angles, as shown in FIG. 5D for example, so that a region masked in one orientation will generally not be masked in another orientation. The multiple masked test images can then be combined in software to generate a complete test image with little or no pixels being masked.

Masking can also be implemented through hardware. For example, a programmable liquid crystal display (LCD) mask can be placed in front of the focal plane of the CCD camera, as shown in FIG. 20. FIG. 20 is schematic illustration of a portion of an inspection module 600 having a wafer holder 602, which holds a wafer 604, a large array, cooled CCD camera 606 and a high resolution fast video lens 608. Camera 606 has a photodetector array 610 having a field of view 612 through lens 608 that covers substantially the entire wafer 604. A programmable LCD mask 614 is positioned between photodetector array 610 and lens 608.

Camera 606 obtains a first test image of wafer 604 with LCD mask 614 turned off such that all pixels in the mask are transparent. Diffraction patterns appear as saturated regions in the first test image. Next, the first test image is electronically mapped on to LCD mask 614. The LCD pixels corresponding to the saturated regions are turned on such that those pixels are opaque. The opaque pixels mask photodetector array 610 at the bright regions. A second test image is then acquired by camera 606 through mask 614. The second test image has diffraction patterns attenuated by masking and may be analyzed using the techniques described above.

Another problem associated with high dynamic range images is that the background noise amplitude varies greatly from pixel to pixel, with the brighter regions of the image generally having a high noise level. When using image processing methods such as reference image comparison or computer filtering referred to above, it is often desirable to use a variable threshold to separate particles and defects from background across the entire image. A higher threshold is generally needed at the brighter regions of the image. Ideally, in the case of high dynamic range images, a CCD camera having a logarithmic response can be used. Alternatively CCD cameras having an anti-blooming function can be used. If a CCD camera with a linear response is used, "gamma" correction can be applied to the test image before subjecting it to image analysis. One scheme would be to reassign pixel brightness levels in the image according to a suitable transfer function. For example a logarithmic function would compress the brightness at the bright end of the scale. This image histogram equalization procedure can improve the signal-to-noise ratio for a high-dynamic range image when using some of the image analysis techniques described above.

14. Conclusion

The optical inspection module of the present invention illuminates the entire surface of a substrate at one time. Images captured by the camera are analyzed in real time by a computer to detect and report flaws and defects. This large-area-illumination and large-area-imaging provides a simple, cheap and compact inspection tool with a minimum of moving parts and which is capable of rapid inspection of substrates under a variety of different illumination and detection modes. The various features and elements of the inspection module provide the module with considerable flexibility in function. The inspection module and methodology discussed above are adaptable for inspection of different types of substrate surfaces such as that of bare wafers, patterned wafers, back sides of wafers, film coated wafers, flat panels, magnetic recording discs, and electronic packaging substrates. The inspection methodology is also flexible enough to permit multiple optical measurement modes, such as light scattering and photo-luminescence. The inspection module is capable of being packaged as a stand-alone, bench-top or integrated metrology system for different applications.

Although the present invention has been described with reference to preferred embodiments, workers skilled in the art will recognize that changes may be made in form and detail without departing from the spirit and scope of the invention.

What is claimed is:

1. An optical inspection module for detecting defects on a surface of a substrate, the module comprising:
    a substrate holding position, wherein the surface of the substrate defines an object plane at the substrate holding position;
    a light source;
    a light beam path extending from the light source to the substrate holding position and having a directional component within the object plane, wherein the light beam path illuminates substantially the entire surface;
    a first lens which is oriented to collect light reflected from the light beam path by the substrate surface, the first lens having a lens plane and an optical axis that is oriented at a first non-zero azimuthal angle to the directional component of the light beam path relative to the object plane; and
    a first photodetector array having a plurality of pixels defining an image plane within a focal plane of the first lens, wherein each pixel corresponds to an area on the surface and the plurality of pixels together form a field of view that covers substantially the entire surface, and wherein the lens plane and the image plane are non-parallel to the object plane;
    a second lens having an optical axis that is oriented at a second, different azimuthal angle to the directional component of the light beam path relative to the object plane;
    a second photodetector array having a plurality of pixels defining, an image plane which is positioned to detect light from the second lens, wherein each pixel corresponds to an area on the surface and the plurality of pixels together form a field of view that covers substantially the entire surface; and
    image analysis means coupled to the first and second photodetector arrays for acquiring first and second test images from the first and second photodetector arrays, respectively, and for identifying a defect on the substrate surface based on a comparison of the first and second test images.

2. The optical inspection module of claim 1 wherein the object plane, the lens plane of the first lens and the image plane of the first photodetector array intersect along a line.

3. The optical inspection module of claim 1 wherein the first lens has an optical axis that is oriented at an oblique angle to the object plane.

4. The optical inspection module of claim 1 wherein the first lens is oriented to collect only non-specularly reflected light that is scattered from the light beam path by any defects on the surface.

5. The optical inspection module of claim 4 wherein the light beam path has a grazing angle of incidence with respect to the surface of the substrate.

6. The optical inspection module of claim 1 wherein the first lens has an optical axis that is oriented relative to the light beam path to detect light that is scattered from the light beam path in a direction selected from the group consisting of forward scattering, backward scattering light and side scattering.

7. The optical inspection module of claim 1 wherein the second lens has a lens plane which intersects with the image plane of the second photodetector array and with the object plane along a line.

8. The optical inspection module of claim 1 wherein the image analysis means comprises means for producing a combined test image based on a combination of the first and second test images.

9. The optical inspection module of claim 1 wherein at least one of the light source, the substrate and a combination of the first photodetector array and the first lens are rotatable about an axis normal to the object plane relative to at least one of the other of the light source, the substrate and a combination of the first photodetector array and the first lens, from a first rotational position to a second, different rotational position.

10. The optical inspection module of claim 1 wherein:
the second lens has a lens plane and a focal plane that are oriented parallel to the object plane; and
the image plane of the second photodetector array is positioned in the focal plane of the second lens and parallel to the object plane.

11. The optical inspection module of claim 1 wherein the light source comprises a uniformly illuminated panel oriented relative to the object plane and opposite to the first lens, relative to the substrate, such that an image collected by the first photodetector array through the first lens includes an image of the substrate surface superimposed on an image of the uniformly illuminated panel.

12. An integrated optical inspection module comprising:
a substrate holder for holding a substrate having a surface;
a first measurement instrument for detecting defects on the substrate surface, which comprises:
  a light source having a light beam port;
  a light beam path extending from the light beam port to the substrate holding position and illuminating substantially the entire substrate surface on the substrate holder;
  a lens which is oriented to collect light reflected from the light beam path by the substrate surface; and
  a photodetector array having a plurality of pixels defining an image plane within a focal plane of the lens, wherein each pixel corresponds to an area on the substrate surface and the plurality of pixels together form a field of view that covers substantially the entire substrate surface; and
a second measurement instrument integrated into the module with the first measurement instrument and comprising a sensor oriented for sensing a physical characteristic of the substrate surface, wherein the sensor is movable between at least one measurement position within the field of view of the first measurement instrument and a retracted, non-measurement position outside of the field of view.

13. The integrated optical inspection module of claim 12 wherein the lens is oriented to collect only non-specularly reflected light that is scattered from the light beam path by any defects on the substrate surface.

14. The integrated optical inspection module of claim 12 wherein:
the substrate holder has a fixed position within the module; and
the first measurement instrument has a fixed position within the module.

15. The integrated optical inspection module of claim 14 wherein the sensor is mounted on an X-Y motion stage.

16. The integrated optical inspection module of claim 12 wherein the sensor is selected from the group consisting of a microscope and a film metrology head.

17. The integrated optical inspection module of claim 12 wherein the sensed physical characteristic is selected from the group consisting of spectral reflectance, refractive index, resistivity, stress, and thickness of a film on the substrate surface.

18. The integrated optical inspection module of claim 12, wherein the module is integrated into a cluster tool comprising:
a substrate load-unload port;
a plurality of substrate processing stations, wherein the first and second measurement instruments are integrated together within one of the substrate processing stations; and
a substrate transport arm which interfaces with each of the substrate processing stations along a substrate travel path.

19. An optical inspection module comprising:
a substrate holding position for holding a substrate having a surface;
a light source which produces an excitation light beam in a first wavelength range;
a light beam path extending from the light source to the substrate holding position and illuminating substantially the entire substrate surface at the substrate holding position with the excitation light beam, whereby compounds on the substrate surface absorb energy from the excitation light beam and emit photons of lower energy in a second, different wavelength range;
a lens;
a photodetector array having a plurality of pixels defining an image plane within a focal plane of the lens, wherein each pixel corresponds to an area on the substrate surface and the plurality of pixels together form a field of view that covers substantially the entire substrate surface; and
an optical filter positioned within an optical path from the substrate to the photodetector array, through the lens, which entirely blocks light reflected from the substrate surface in the first wavelength range and transmits light emitted from the substrate surface in the second wavelength range.

20. The optical inspection module of claim 19 wherein the light beam path has a grazing angle of incidence with respect to the substrate surface.

21. The optical inspection module of claim 19 wherein the first wavelength range includes ultraviolet light.

22. The optical inspection module of claim 19 wherein the light source is selected from the group consisting of an arc lamp, a flash lamp and a laser.

23. A method of inspecting a surface of a substrate, the method comprising:
(a) illuminating substantially the entire substrate surface with a light beam;
(b) applying light reflected from the light beam by any defects or other features on the substrate surface to a photodetector array having a plurality of pixels, wherein each pixel corresponds to a unit area on the surface and the plurality of pixels together have a field of view covering substantially the entire surface;
(c) producing a digital test image having a plurality of pixels with intensities that are functions of intensities of the reflected light applied to corresponding pixels in the photodetector array;

(d) applying a digital convolution filter to the digital test image to produce a filtered test image having a plurality of pixels; and (e) comparing intensity of pixels of the filtered test image to a respective intensity threshold value.

24. The method of claim 23 wherein step (a) comprises illuminating substantially the entire substrate surface with the light beam oriented at a grazing angle of incidence with respect to the surface.

25. The method of claim 23 wherein step (b) comprises applying only non-specularly reflected light that is scattered from the light beam by any defects or other features on the substrate surface to the photodetector array.

26. The method of claim 23 wherein the respective intensity threshold value varies from one set of the plurality of pixels in the filtered test image to another set of the plurality of pixels in the filtered test image.

27. The method of claim 26 wherein the respective intensity threshold value applied to a given set of pixels varies according to a type and location of features on the substrate surface imaged by those pixels.

28. The method of claim 23 and further comprising:

(f) producing an error image having a plurality of pixels, wherein each pixel in the error image identifies whether the intensity of a corresponding pixel in the filtered test image exceeds the respective intensity threshold value; and (g) identifying any defects on the substrate surface as a function of the error image.

29. The method of claim 28 wherein the substrate comprises an unpatterned semiconductor wafer and step (g) comprises identifying any defects on the surface of the unpatterned semiconductor wafer as a function of the error image.

30. The method of claim 23 wherein step (d) comprises applying a digital Laplacian filter to the digital test image to produce the filtered test image.

31. A method of inspecting a surface of a substrate, the method comprising:

(a) illuminating substantially the entire substrate surface;

(b) applying light reflected by any defects or other features on the substrate surface to a photodetector array having a plurality of pixels, wherein each pixel corresponds to a unit area on the surface and the plurality of pixels together have a field of view covering substantially the entire surface;

(c) producing a digital test image having a plurality of pixels, wherein each pixel has an intensity that is a function of an intensity of the reflected light applied to a corresponding pixel in the photodetector array;

(d) for each pixel in the digital test image, producing a corresponding pixel in a reference image having an intensity equal to a mathematical function of the intensities of a plurality of the pixels in the digital test image that surround that pixel;

(e) subtracting the reference image from the digital test image to produce a difference image having a plurality of pixels; and (f) comparing intensity of pixels in the difference image to a respective intensity threshold value.

32. The method of claim 31 wherein:

step (a) comprises illuminating substantially the entire substrate surface with a light beam oriented at a grazing angle of incidence with respect to the surface; and step (b) comprises applying only non-specularly reflected light that is scattered from the light beam by any defects on the substrate surface to the photodetector array.

33. The method of claim 31 wherein in step (d) the mathematical function is a mathematical median function.

34. The method of claim 31 wherein the respective intensity threshold value varies from one set of the plurality of pixels in the difference image to another set of the plurality of pixels in the difference image.

35. The method of claim 34 wherein the respective intensity threshold value applied to a given set of pixels varies according to a type and location of features on the substrate surface imaged by those pixels.

36. The method of claim 31 and further comprising:

(g) producing an error image having a plurality of pixels, wherein each pixel in the error image identifies whether the intensity of a corresponding pixel in the difference image exceeds the respective intensity threshold value; and (h) identifying any defects on the substrate surface as a function of the error image.

37. The method of claim 36 wherein the substrate comprises a patterned semiconductor wafer and step (g) comprises identifying any defects on the surface of the patterned semiconductor wafer as a function of the error image.

38. A method of inspecting a surface of a patterned substrate having a substrate surface with a background pattern, the method comprising:

(a) illuminating substantially the entire substrate surface;

(b) applying light reflected from the substrate by any defects or other features on the substrate surface to a photodetector array having a plurality of pixels, wherein each pixel corresponds to a unit area on the surface and the plurality of pixels together have a field of view covering substantially the entire surface;

(c) producing a digital test image having a plurality of pixels, wherein each pixel has an intensity that is a function of an intensity of the reflected light applied to a corresponding pixel in the photodetector array;

(d) applying a digital fast Fourier transform to the digital test image to produce a transform image;

(e) filtering the transform image to produce a filtered transform image in which features produced in the transform image by repeating patterns of the substrate surface are removed; and (f) applying a digital inverse fast Fourier transform to the filtered transform image to produce a re-created image of the substrate surface with the repeating patterns filtered out.

39. The method of claim 38 wherein:

step (a) comprises illuminating substantially the entire substrate surface with a light beam oriented at a grazing angle of incidence with respect to the surface; and step (b) comprises applying only non-specularly reflected light that is scattered from the light beam by any defects on the substrate surface to the photodetector array.

40. The method of claim 38 and further comprising:

(g) comparing intensity of pixels in the re-created image to a respective intensity threshold value.

41. The method of claim 40 wherein the respective intensity threshold value varies from one set of the plurality of pixels in the re-created image to another set of the plurality of pixels in the re-created image.

42. The method of claim 41 wherein the respective intensity threshold value applied to a given set of pixels varies according to a type and location of features on the substrate surface imaged by those pixels.

43. The method of claim 40 and further comprising:
(h) producing an error image having a plurality of pixels, wherein each pixel in the error image identifies whether the intensity of a corresponding pixel in the re-created image exceeds the respective intensity threshold value; and
(i) identifying any defects on the substrate surface as a function of the error image.

44. A method of inspecting a surface of a patterned substrate having a substrate surface with a background pattern, the method comprising:
(a) illuminating substantially the entire substrate surface with a light beam;
(b) applying non-specularly reflected light that is scattered from the light beam by any defects on the substrate surface to a photodetector array having a plurality of pixels, wherein each pixel corresponds to a unit area on the surface and the plurality of pixels together have a field of view covering substantially the entire surface;
(c) producing a digital test image having a plurality of pixels, wherein each pixel has an intensity that is a function of an intensity of the scattered light applied to a corresponding pixel in the photodetector array;
(d) applying a first image filtering process to the digital test image to produce a first defect pixel map;
(e) applying a second image filtering process to the digital test image to produce a second defect pixel map; and
(f) combining each pixel of the first defect pixel map with a corresponding one of the pixels in the second defect pixel map to produce a corresponding pixel in a combined defect pixel map.

45. The method of claim 44 wherein:
each pixel in the first defect pixel map comprises a binary value indicating whether a defect exists within a corresponding unit area on the substrate surface;
each pixel in the second defect pixel map comprises a binary value indicating whether a defect exists within a corresponding unit area on the substrate surface; and
step (f) comprises combining each pixel of the first defect pixel map with a corresponding one of the pixels in the second defect pixel map according to a logical AND function to produce the corresponding pixel in the combined defect pixel map.

46. The method of claim 44 wherein:
each pixel in the first defect pixel map comprises a binary value indicating whether a defect exists within a corresponding unit area on the substrate surface;
each pixel in the second defect pixel map comprises a binary value indicating whether a defect exists within a corresponding unit area on the substrate surface; and
step (f) comprises combining each pixel of the first defect pixel map with a corresponding one of the pixels in the second defect pixel map according to a logical OR function to produce the corresponding pixel in the combined defect pixel map.

47. The method of claim 44 wherein:
step (f) comprises combining each pixel of the first defect pixel map with a corresponding one of the pixels in the second defect pixel map according to a weighted combinatory function to produce the corresponding pixel in the combined defect pixel map.

48. The method of claim 44 wherein one of steps (d) and (e) comprises:
(g)(1) applying a digital convolution filter to the digital test image to produce a filtered test image having a plurality of pixels; and
(g)(2) comparing each pixel in the filtered test image to a respective intensity threshold to produce a corresponding one of the pixels in the respective first or second defect pixel map.

49. The method of claim 44 wherein one of steps (d) and (e) comprises:
(g)(1) for each pixel in the digital test image, producing a corresponding pixel in a reference image having an intensity equal to a mathematical function of the intensities of a plurality of the pixels in the digital test image that surround that pixel;
(g)(2) subtracting the reference image from the digital test image to produce a difference image having a plurality of pixels; and
(g)(3) comparing each pixel in the difference image to a respective intensity threshold to produce a corresponding one of the pixels in the respective first or second defect pixel map.

50. The method of claim 49 wherein in step (g)(1) wherein the mathematical function is a mathematical median function.

51. The method of claim 44 wherein one of steps (d) and (e) comprises:
(g)(1) applying a digital fast Fourier transform to the digital test image to produce a transform image;
(g)(2) filtering the transform image to produce a filtered transform image in which features produced in the transform image by repeating patterns of the substrate surface are removed;
(g)(3) applying a digital inverse fast Fourier transform to the filtered transform image to produce a re-created image of the substrate surface with the repeating patterns filtered out; and
(g)(4) comparing each pixel in the recreated image to a respective intensity threshold to produce a corresponding one of the pixels in the respective first or second defect pixel map.

52. The method of claim 44 and further comprising:
(g) masking at least one of the first and second defect maps with a binary mask filter having a respective binary masking value for each pixel in the first and second defect maps to produce a respective masked defect map, wherein the binary masking values vary from one set of pixels in the binary mask filter to another set of pixels in the binary mask filter according to a type and location of features on the substrate surface imaged by those pixels; and
(h) performing step (f) with the respective masked defect map.

* * * * *